United States Patent
Pereira et al.

(10) Patent No.: US 7,217,424 B2
(45) Date of Patent: May 15, 2007

(54) COMPOSITIONS CONTAINING ESTERS OF AROMATIC ALKOXYLATED ALCOHOLS AND FATTY CARBOXYLIC ACIDS

(75) Inventors: Abel Pereira, Belleville, NJ (US); Christopher Westergom, Hillsborough, NJ (US); Patrick Obukowho, Fords, NJ (US)

(73) Assignee: Croda, Inc., Parsippany, NJ (US)

( * ) Notice: Subject to any disclaimer, the term of this patent is extended or adjusted under 35 U.S.C. 154(b) by 0 days.

(21) Appl. No.: 10/272,556

(22) Filed: Oct. 16, 2002

(65) Prior Publication Data

US 2003/0161792 A1 Aug. 28, 2003

Related U.S. Application Data

(60) Provisional application No. 60/330,208, filed on Oct. 17, 2001.

(51) Int. Cl.
*A61K 7/00* (2006.01)

(52) U.S. Cl. .......................... 424/401; 424/59; 424/65; 554/227; 554/228; 554/229

(58) Field of Classification Search ................ 424/401, 424/59, 65; 554/227, 228, 229
See application file for complete search history.

(56) References Cited

U.S. PATENT DOCUMENTS

| | | | |
|---|---|---|---|
| 1,985,424 A | 12/1934 | Piggott | |
| 2,438,091 A | 3/1948 | Lynch | |
| 2,528,378 A | 10/1950 | Mannheimer | |
| 2,658,072 A | 11/1953 | Kosmin | |
| 2,703,798 A | 3/1955 | Schwartz | |
| 2,965,576 A | 12/1960 | Wilson | |
| 3,155,591 A | 11/1964 | Hilfer | |
| 3,337,490 A | 8/1967 | Aron | |
| 3,755,560 A | 8/1973 | Dickert et al. | |
| 3,929,678 A | 12/1975 | Laughlin et al. | |
| 3,959,461 A | 5/1976 | Bailey et al. | |
| 4,185,017 A | 1/1980 | Piesch et al. | |
| 4,275,055 A | 6/1981 | Nachtigal et al. | |
| 4,275,222 A | 6/1981 | Scala, Jr. | |
| 4,278,655 A | 7/1981 | Elmi | |
| 4,293,544 A | 10/1981 | Elmi | |
| 4,322,545 A | 3/1982 | Scala, Jr. | |
| 4,323,693 A | 4/1982 | Scala, Jr. | |
| 4,323,694 A | 4/1982 | Scala, Jr. | |
| 4,387,090 A | 6/1983 | Bolich, Jr. | |
| 4,421,769 A | 12/1983 | Dixon et al. | |
| 4,557,853 A | 12/1985 | Collins | |
| 4,659,757 A | 4/1987 | Okamoto et al. | |
| 4,704,272 A | 11/1987 | Oh et al. | |
| 4,741,855 A | 5/1988 | Grote et al. | |
| 4,788,006 A | 11/1988 | Bolish, Jr. et al. | |
| 4,791,097 A | 12/1988 | Walele et al. | |
| 4,902,499 A | 2/1990 | Bolish, Jr. et al. | |
| 4,919,934 A | 4/1990 | Deckner et al. | |
| 4,976,953 A | 12/1990 | Orr et al. | |
| 5,011,681 A | 4/1991 | Ciotti et al. | |
| 5,120,532 A | 6/1992 | Wells et al. | |
| 5,151,209 A | 9/1992 | McCall et al. | |
| 5,151,210 A | 9/1992 | Steuri et al. | |
| 5,270,461 A | 12/1993 | Walele et al. | |
| 5,271,930 A | 12/1993 | Walele et al. | |
| 5,302,377 A * | 4/1994 | Pereira et al. | 424/59 |
| 5,455,025 A * | 10/1995 | Pereira et al. | 424/59 |
| 5,597,555 A * | 1/1997 | Pereira et al. | 424/59 |
| 5,693,316 A * | 12/1997 | Pereira et al. | 424/59 |
| 5,959,130 A | 9/1999 | Walele et al. | |
| 6,300,390 B1 | 10/2001 | Angeletakis | |
| 6,599,936 B1 * | 7/2003 | Bajor et al. | 514/532 |
| 6,987,195 B2 | 1/2006 | Pereira et al. | 554/227 |

FOREIGN PATENT DOCUMENTS

EP 0 095 238 A2 11/1983

* cited by examiner

*Primary Examiner*—Sreenivasan Padmanabhan
*Assistant Examiner*—Konata M. George
(74) *Attorney, Agent, or Firm*—Lerner, David, Littenberg, Krumholz & Mentlik, LLP

(57) ABSTRACT

A personal care or cosmetic product composition that includes from about 0.1% to about 99% of at least one ester of alkoxylated aromatic alcohol and fatty carboxylic acid, and from about 0.1% to 60% of at least one functional ingredient is provided. The functional ingredients in the composition may include active ingredients and additional ingredients. Especially suitable active ingredients are sunscreen active ingredients and antiperspirant active ingredients. Preferred compositions are sunscreen product formulations and antiperspirant products. In one preferred embodiment, the composition further includes at least one cyclomethicone compound present in the amount of from about 1% to 99% by weight of the composition. A method of improving the protection of human or animal skin or hair from radiation and a method of improving the protection of human or animal skin or hair from perspiration are also provided.

135 Claims, No Drawings

COMPOSITIONS CONTAINING ESTERS OF AROMATIC ALKOXYLATED ALCOHOLS AND FATTY CARBOXYLIC ACIDS

CROSS-REFERENCE TO RELATED APPLICATIONS

This patent application claims the benefit of the filing date of the U.S. Provisional Application No. 60/330,208, filed Oct. 17, 2001, the disclosure of which is hereby incorporated by reference in its entirety.

FIELD OF THE INVENTION

The present invention relates to the field of chemical manufacture and in particular, cosmetics and personal care products.

BACKGROUND OF THE INVENTION

Formulation of personal care and cosmetic products, such as shampoos, conditioners, sunscreen lotions, lipstick products, mascara, and the like, presents a number of challenges. The feel and look of such products should appeal to consumers. For example, it may be desirable for certain of such products to have a non-greasy skin feel, good skin-spread ability, pleasant smell, and so on. At the same time, the cosmetic and personal care products typically include a variety of necessary ingredients. For the formulator, the necessity of obtaining physical characteristics that appeal to consumers coexists with the necessity of incorporating the necessary functional ingredients in the product.

Personal care and cosmetic products typically include chemical compounds that function as emollients. The emollients contribute to the desired skin feel, but often serve other purposes in the formulation as well.

Emollients, which often constitute a major portion of the product formulation, can also significantly influence the dissolution/dispersion of the functional ingredients in the formulation. For example, the sunscreen products include sunscreen active ingredients that are preferably uniformly dissolved or dispersed in the formulation. However, certain commonly used sunscreen active ingredients exhibit poor solubility/dispersability in the product formulations. Any non-uniform distribution of the active ingredient may lead to a reduction in the quality and performance of the sunscreen product. Likewise, many cosmetic and personal care products contain fragrances, which also may exhibit poor solubility/dispersability, making it difficult to incorporate the fragrances in the product formulation. Therefore, the emollient component of the product formulation should not negatively effect the solubility of the functional ingredient(s), and, preferably, should help solubilize or disperse the functional ingredient(s) in the formulation.

Certain aromatic esters are presently used as ingredients in the personal care and cosmetic products. For example, Croda Corporation of Parsippany, N.J., manufactures and sells alkoxylated esters of aromatic dicarboxylic and tricarboxylic acids, which are disclosed in U.S. Pat. Nos. 5,693,316, 5,597,555, 5,455,025, and 5,302,377. The aromatic compounds disclosed in these patents are esters of aromatic carboxylic acids, and thus contain an ester carboxylic group

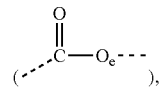

in which the aromatic nucleus (Ar) is connected to the carbon atom of the ester carboxylic group, and the fatty alkyl group (R) is connected to the ester oxygen atom ($O_e$) of the ester carboxylic group. Thus, the overall order of connection to the ester carboxylic group in these esters may be illustrated as:

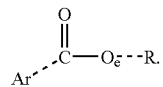

Although these esters are excellent emollients for sunscreens and cosmetics, the need still exists for new compounds useful as ingredients for personal care and cosmetic products to provide additional options to the product formulators. Specifically, the need exists for emollient compounds that improve the solubility of active ingredients in the formulation while contributing to a pleasant skin feel.

SUMMARY OF THE INVENTION

In accordance with one preferred aspect, the present invention addresses these needs by providing esters of aromatic alkoxylated alcohols and fatty carboxylic acids, which are excellent additives for cosmetic and personal care products. For example, they may be used as emollients, solubilizers/diluents and/or thickeners. Preferably, the esters of aromatic alkoxylated alcohol and fatty carboxylic acid are compounds that include an aromatic nucleus (Ar), an alkoxy spacer (Alk), an ester carboxylic group

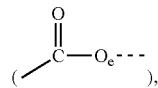

and a fatty alkyl group (R), with the aromatic nucleus being connected to the ester oxygen atom ($O_e$) of the ester carboxylic group via the alkoxy spacer and the fatty alkyl group being attached to the carbon atom of said ester carboxylic group. The overall order of connection to the ester carboxylic group(s) in the esters of the invention may be illustrated as

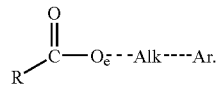

Thus, the structure of the aromatic esters of the invention is substantially different from the structure of the esters disclosed in U.S. Pat. Nos. 5,693,316, 5,597,555, 5,455,025, and 5,302,377.

The esters of aromatic alkoxylated alcohols and fatty carboxylic acids preferably have one or two ester carboxylic groups. The fatty alkyl group (R) of the esters of the invention preferably contain from 1 to 39 carbon atoms. The preferred esters of aromatic alkoxylated alcohols and fatty carboxylic acids have a skin spread factor of less than 10 or a viscosity of less than 20,000 cps. Various preferred esters of aromatic alkoxylated alcohols and fatty carboxylic acids are also disclosed herein.

In accordance with another preferred aspect, the invention provides a personal care or cosmetic product composition that includes a) at least one ester of alkoxylated aromatic alcohol and fatty carboxylic acid present in the amount of from about 0.1% to about 99% by weight of the composition and b) at least one functional ingredient present in the amount of from about 0.1% to 60% by weight of the composition. The functional ingredients may include active ingredients and additional ingredients. Preferred compositions are sunscreen product formulations and antiperspirant products. Thus, especially suitable active ingredients are sunscreen active ingredients and antiperspirant active ingredients.

In one preferred embodiment of this aspect of the invention, the composition further includes at least one cyclomethicone compound present in the amount of from about 1% to 99% by weight of the composition.

In accordance with yet another preferred aspect, the invention provides a method of improving the protection of human or animal skin or hair from radiation by providing a sunscreen product formulation including a sunscreen active ingredient and at least one ester of alkoxylated aromatic alcohol and fatty carboxylic acid, and topically applying such sunscreen product formulation to the hair or skin.

In accordance with yet another preferred aspect, the invention provides a method of improving the protection of human or animal skin or hair from perspiration by providing a antiperspirant product formulation including an antiperspirant active ingredient, at least one cyclomethicone compound and at least one ester of alkoxylated aromatic alcohol and fatty carboxylic acid, and topically applying such antiperspirant product formulation to the hair or skin.

DESCRIPTION OF THE PREFERRED EMBODIMENTS

For the purposes of the present invention, various terms used herein are defined as follows. A "compound" is a distinct chemical substance having molecules of the same chemical structure. A "compound" is not a mixture of molecules having different chemical structures. A "composition" may include one compound or a mixture of compounds. An "alkyl" group is a group that includes a chain of carbon atoms. An alkyl group may terminate in alkyl or non-alkyl functionality and may connect to the rest of the molecule through alkyl or non-alkyl functionality. In the compounds described herein, and consistent with the definitions set forth above, the alkyl groups, when present, may be substituted or unsubstituted, straight chain or branched, saturated or unsaturated. The term "fatty" in reference to alkyl groups and/or carboxylic acids is not intended to indicate origin. Rather, the term "fatty" is used in reference to any group that provides the esters of the invention with hydrophobic contribution. Purely for the purpose of illustration, the methyl group of the acetic acid is a fatty group within the meaning of the invention. The substituents of the alkyl groups described herein, if present, may include lower alkyl, which are alkyl groups containing from 1 to 8 carbon atoms, such as methyl, ethyl, n-propyl, i-propyl, and butyl; halogenated lower alkyl, such as trifluoromethyl, perfluoroethyl, chloromethyl, and dichloromethyl; arylalkyl, such as benzyl; alkylaryl, such as p-methylbenzyl; halo, such as fluoro, chloro and bromo; carboxy, such as acetoxy and ethylcarboxy; alkylcarboxy, such as acetoxymethyl and acetoxyethyl; arylacetoxy, such as acetylbenzyl; hydroxy; alkoxy, such as methoxy, ethoxy and propoxy; and alkylhydroxy, such as hydroxymethyl and hydroxyethyl.

The "alkoxylated aromatic alcohols" include compounds having one, two or more hydroxyl groups —OH, which are referred to herein as the hydroxy groups. The alkoxylated aromatic alcohols containing a single hydroxy group are referred to as monohydroxy alkoxylated aromatic alcohols. Purely for the purposes of illustration, monohydroxy alkoxylated aromatic alcohols include compounds having a single group of the structure $\text{-}[\text{CH}_2\text{CH}_2\text{O}]_5\text{H}$ and no other hydroxy groups in the molecule. The alkoxylated aromatic alcohols containing two hydroxy groups are referred to as dihydroxy alkoxylated aromatic alcohols. Purely for the purposes of illustration, dihydroxy alkoxylated aromatic alcohols include compounds having two groups of the structure $\text{-}[\text{CH}_2\text{CH}_2\text{O}]_5\text{H}$ and no other hydroxy groups in the molecule, as well as compounds having one group of the structure $\text{-}[\text{CH}_2\text{CH}_2\text{O}]_5\text{H}$ one group of the structure $\text{-CH}_2\text{-OH}$, and no other hydroxy groups in the molecule.

The term "an ester of alkoxylated aromatic alcohol and fatty carboxylic acid," which is used in defining the compounds of the invention, is the common name for the class of esters compounds. The esters of the invention are defined by the nature of the groups connected to the ester group. It should be understood that the esters of the invention may be produced by any methods known in the art, rather than exclusively from the alkoxylated aromatic alcohols and the fatty carboxylic acids. The esters of the invention include several groups of compounds, such as monoesters of monocarboxylic acids and monohydroxy alkoxylated aromatic alcohols, monoesters of monocarboxylic acids and dihydroxy alkoxylated aromatic alcohols, and diesters of monocarboxylic acids and dihydroxy alkoxylated aromatic alcohols. While certain other types of compounds are not excluded, the polyesters and oligoesters are not the esters of alkoxylated aromatic alcohol and fatty carboxylic acid within the meaning of the invention. For example, the products of the condensation reaction between a dicarboxylic acid (or a dicarboxy derivative of a dicarboxylic acid) and a dihydroxy alkoxylated aromatic alcohol are not the esters of alkoxylated aromatic alcohol and fatty carboxylic acid within the meaning of the invention.

The preferred esters of alkoxylated aromatic alcohol and fatty carboxylic acid have the structure

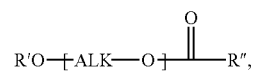

where R' is an organic moiety that contains at least one aromatic nucleus $R_N$; R" is a fatty alkyl group; and $\text{-}[\text{ALK-O}]\text{-}$ is an alkoxy spacer.

The aromatic nucleus $R_N$ may contain from 6 to 20 carbon atoms exclusive of substitution. Nuclei $R_N$ having 6 and 10 carbon atoms are preferred. Non-limiting examples of the aromatic nuclei $R_N$ are benzene, naphthalene and anthracene nuclei, which contain 6, 10 and 14 carbon atoms, respectively. The structures of the benzene, naphthalene and anthracene nuclei are illustrated below, with the carbon atoms available for substitution numbered according to the accepted nomenclature:

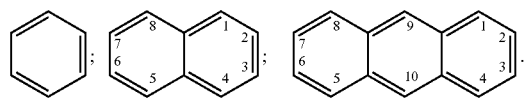

The group R' may contain substituted or unsubstituted aromatic nuclei $R_N$. Non-limiting examples of the substituents that may be present in the aromatic nucleus $R_N$, include lower alkyl, such as methyl, ethyl, n-propyl, i-propyl, and butyl; aryl; arylalkyl; alkylaryl; halo, such as fluoro, chloro and bromo; acetoxy; alkylacetoxy; arylacetoxy; carboxy; alkylcarboxy; hydroxy; alkoxy; such as methoxy, ethoxy and propoxy; and alkylhydroxy.

The aromatic nucleus $R_N$ of the group R' is connected to the alkoxy spacer $-[ALK-O]-$. The aromatic nucleus $R_N$ may be directly attached to the alkoxy spacer. However, in one preferred embodiment, the group R' has the structure $R_N-(CH_p)_n-$, where $-(CH_p)_n-$ is a group which connects the nucleus $R_N$ to the alkoxy spacer. The group $-(CH_p)_n-$ may be straight-chain or branched, saturated or unsaturated; p is 0, 1, or 2, and n may vary from 1 to 6. In another variant, the group R' has the structure $R_N-O-(CH_p)_q-$, where $-O-(CH_p)_q-$ is the group, which connects the nucleus $R_N$ to the alkoxy spacer. The group $-O-(CH_p)_q-$ may be straight-chain or branched, saturated or unsaturated; p is 0, 1, or 2, and q may vary from 1 to 8.

The group R' may contain one, two, three or more aromatic nuclei $R_N$. Non-limiting examples of the groups R' containing a single aromatic nucleus $R_N$ are

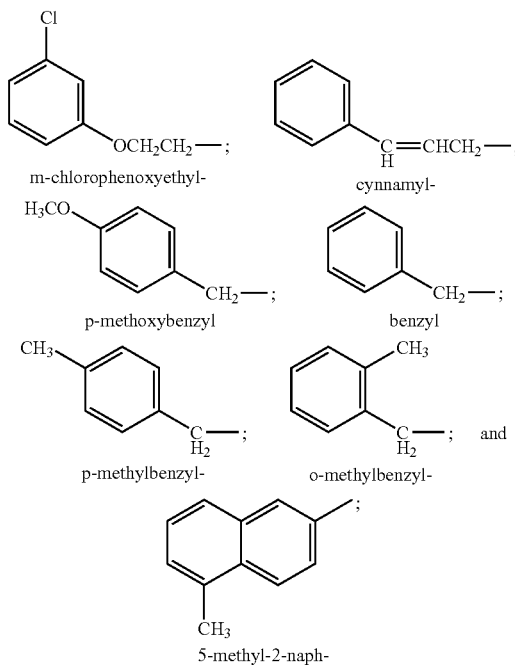

Non-limiting examples of the groups R' containing two aromatic nuclei $R_N$ are

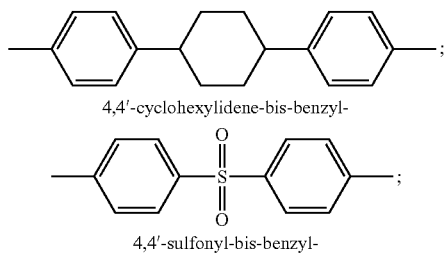

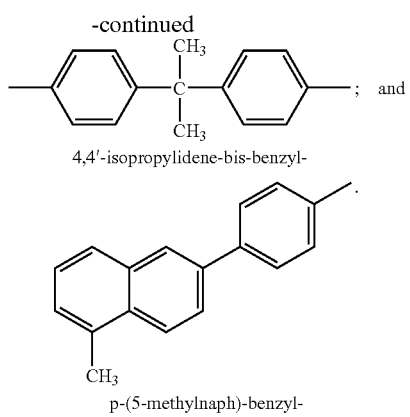

A non-limiting example of the groups R' containing three aromatic nuclei $R_N$ is

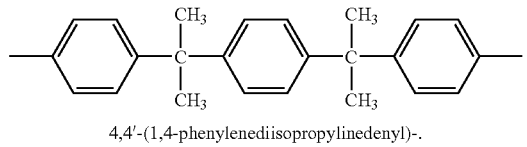

The alkoxy spacer $-[ALK-O]-$ has m number of units of the structure $-(R'''O)_m-$, which may be same or different, with each R''' being an alkyl group, straight-chain or branched, saturated or unsaturated, substituted or unsubstituted, having from 1 to 6 carbon atoms, and m may range from 1 to 300, inclusive. Preferably, the alkoxy spacer $-[ALK-O]-$ includes x number of ethoxy units of the structure $-[CH_2CH_2O]-$ and y number of propoxy units of the structure

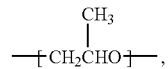

which may be present in any structural order, such as in blocks, randomly or in alternating pattern. In describing the esters of the invention, the structure of the alkoxy spacer may be shown as, for example,

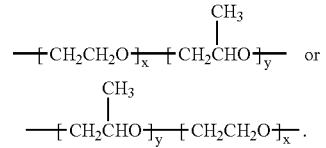

Such depiction indicates only the number of ethoxy and propoxy units, and does not indicate the nature of attachment of the alkoxy spacer to the group R' or the ester group. Further, such depictions of the alkoxy spacer, unless specifically stated, are not intended to indicate the structural order of the ethoxy and propoxy units. For example, the spacer shown as

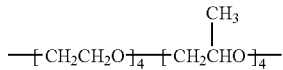

does not indicate a block of 4 ethoxy groups attached to a block of 4 propoxy groups. It does mean, however, that the alkoxy spacer having 4 ethoxy and 4 propoxy units is contemplated.

Preferably, the alkoxy spacer ‒[ALK—O]‒ contains only epoxy and propoxy units, i.e., m is equal to the sum of x and y; x ranges from 0 to 150, inclusive; y ranges from 0 to 150, inclusive; and the sum of x and y ranges from 1 to 300, inclusive. The organization and quantity of the ethoxy and propoxy groups may have substantial effect on the properties of the ester. Thus, for certain application, such as for use as emollients, esters having the sum of x and y which is less than 20 are preferred. In one group of such esters, x is equal to 0. In another group of such esters, y is equal to 0. In yet another group of such esters, x>0, y>0, and x>y. In yet another group of such esters, x>0, y>0, and y>x. For other applications, such as for use as thickeners, the esters having the sum of x and y greater than 100 are preferred.

The fatty alkyl group R″ may be straight chain or branched, saturated or unsaturated, substituted or unsubstituted, and may contain from 1 to 39 carbon atoms. More preferably, the fatty alkyl group R″ does not include an aromatic group. More preferred are aliphatic groups R″ containing from 1 to 21 carbon atoms. Yet more preferred are the R″ groups containing 5 to 21 carbon atoms. Most preferably, 7 to 17 carbon atoms are found in the group R″.

The more preferred esters of alkoxylated aromatic alcohols and fatty carboxylic acids are the compounds of the formulas (I), (II), or (III):

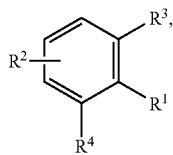
(I)

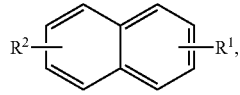
(II)

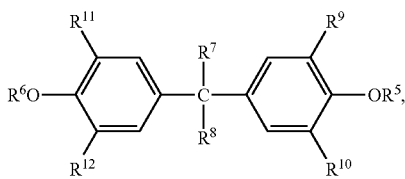
(III)

where $R^1$ is a group of the structure

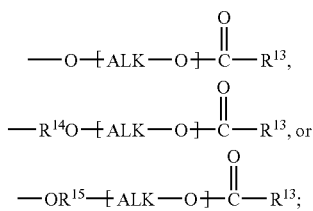

$R^2$, $R^3$, and $R^4$, which may be same or different, are independently hydrogen, lower alkyl, lower halogenated alkyl, hydroxy, lower alkylhydroxy, halo, lower alkoxy,

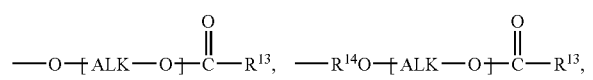

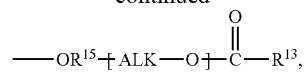

—O—[ALK—O]—H, —$R^{14}$O—[ALK—O]—H, —O$R^{15}$—[ALK—O]—H,

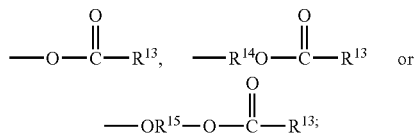

$R^5$ is

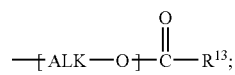

$R^6$ is lower alkyl, —[ALK—O]—H,

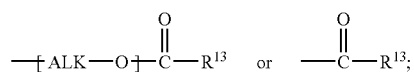

$R^7$ and $R^8$, which may be same or different, are independently hydrogen, halo, lower alkyl, aryl, lower alkoxy, or lower halogenated alkyl;

$R^9$, $R^{10}$, $R^{11}$, and $R^{12}$, which may be same or different, are independently hydrogen, halo, lower alkyl, lower alkoxy, and lower halogenated alkyl;

$R^{13}$, which may be same or different in each of the groups $R^1$, $R^2$, $R^3$, $R^4$, $R^5$, and $R^6$, is an alkyl group, straight chain or branched, saturated or unsaturated, substituted or unsubstituted, having 1 to 39 carbon atoms, preferably, 1 to 21 carbon atoms, more preferably, 5 to 21 carbon atoms, most preferably, 7 to 17 carbon atoms;

$R^{14}$, which may be same or different in each of the groups $R^1$, $R^2$, $R^3$, and $R^4$, is an alkyl group, straight chain or branched, saturated or unsaturated, substituted or unsubstituted, containing 1 to 6 carbon atoms, preferably, —$R^{14}$— is the group —(CH$_p$)$_n$—, in which p is 0, 1, or 2, and n varies from 1 to 6;

$R^{15}$, which may be same or different in each of the groups $R^1$, $R^2$, $R^3$, and $R^4$, is an alkyl group, straight chain or branched, saturated or unsaturated, substituted or unsubstituted, containing 1 to 8 carbon atoms, preferably, —$R^{15}$— is the group —(CH$_p$)$_q$—, in which p is 0, 1, or 2, and q varies from 1 to 8;

—[ALK—O]— is an alkoxy spacer that includes x number of ethoxy units of the structure —[CH$_2$CH$_2$O]— and y number of propoxy units of the structure

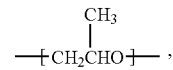

which may be present in any structural order, such as in blocks, randomly or in alternating pattern; each of x and y may be same or different in each of the groups $R^1$, $R^2$, $R^3$, $R^4$, $R^5$ and $R^6$; x ranges from 0 to 150, inclusive; y ranges from 0 to 150, inclusive; and the sum of x and y ranges from 1 to 300, inclusive.

The esters of the formula (I)

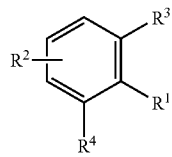
(I)

are derivatives of alkoxylated aromatic alcohols having a single benzene ring. In the more preferred esters of the formula (I), $R^1$ is

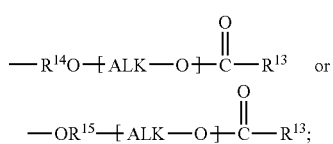

$R^2$ is hydrogen,

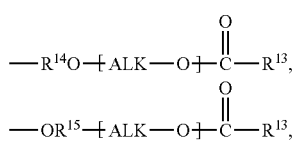

—$R^{14}$O—[ALK—O]—H or —O$R^{15}$—[ALK—O]—H, and $R^3$ and $R^4$ are independently hydrogen, lower alkyl and halogenated lower alkyl. For esters in which $R^2$ is not hydrogen, the para substitution is preferred. However, preferably, $R^2$ is hydrogen, and $R^3$ and $R^4$ are independently hydrogen, methyl, ethyl or propyl.

Non-limiting examples of the esters of the formula (I) are

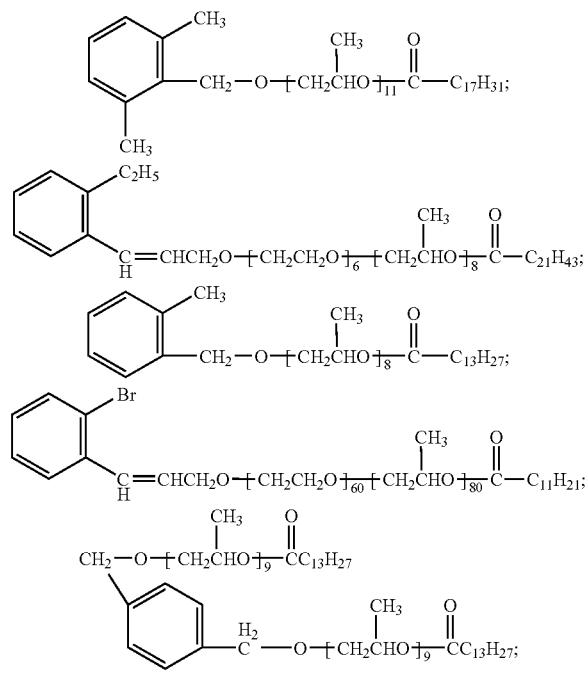

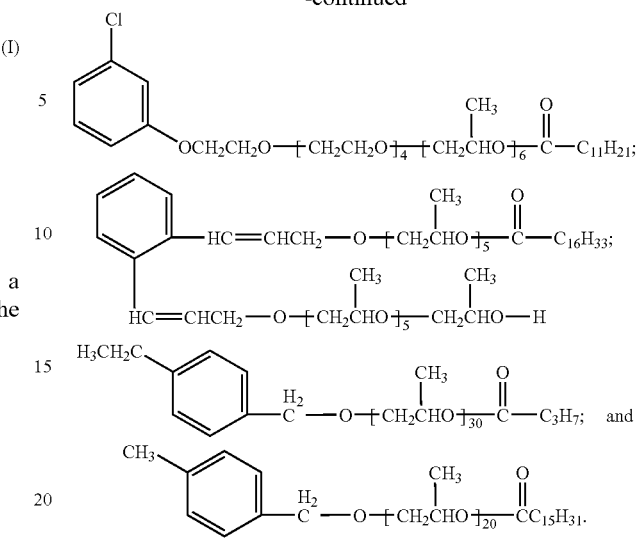

The esters of ethoxylated and/or propoxylated phenoxyethanol:

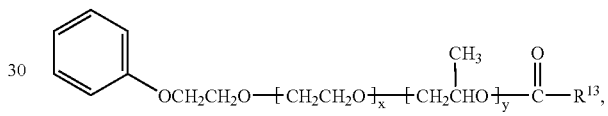

and ethoxylated and/or propoxylated cynnamyl alcohol:

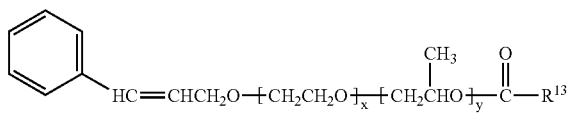

are among the more preferred esters of the formula (I).

Non-limiting examples of the esters of alkoxylated phenoxyethanol are

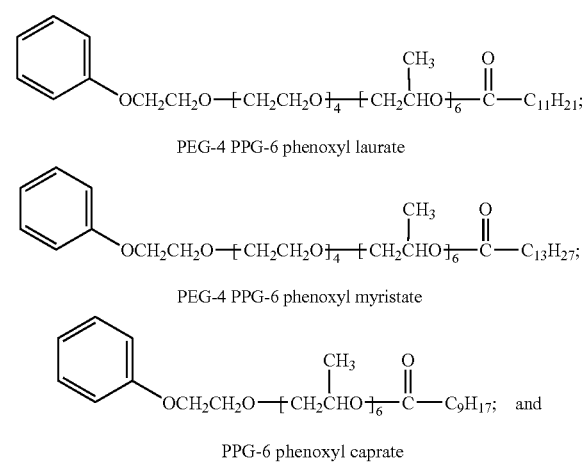

PEG-4 PPG-6 phenoxyl laurate

PEG-4 PPG-6 phenoxyl myristate

PPG-6 phenoxyl caprate

-continued

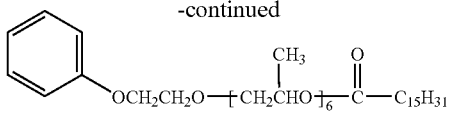

PPG-6 phenoxyl palmitate.

Non-limiting examples of the esters of alkoxylated cynnamyl alcohol are

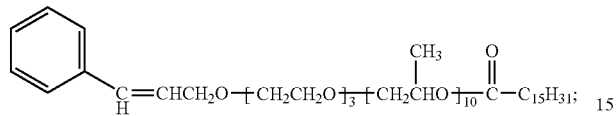

PEG-3 PPG-10 cynnamyl palmitate

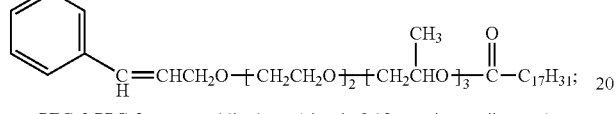

PEG-2 PPG-3 cynnamyl linoleate (cis, cis-9,12-octadecanodienoate)

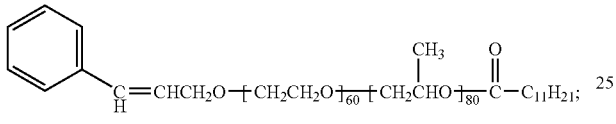

PEG-60 PPG-80 cynnamyl laurate

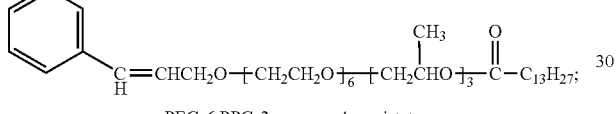

PEG-6 PPG-3 cynnamyl myristate
and

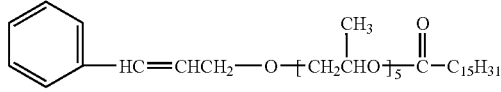

PPG-5 cynnamyl palmitate.

The esters of ethoxylated and/or propoxylated benzyl alcohol are especially preferred:

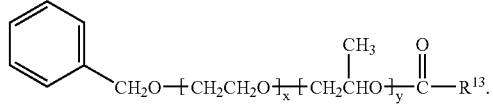

In one preferred variant of these esters, x ranges from 0 to 40, inclusive, y ranges from 0 to 40, inclusive, and the sum of x and y is from 1 to 40, inclusive; more preferably, x ranges from 0 to 30, inclusive, y ranges from 0 to 30, inclusive, and the sum of x and y is from 1 to 30, inclusive; yet more preferably, x ranges from 0 to 20, inclusive, y ranges from 0 to 20, inclusive, and the sum of x and y is from 1 to 20, inclusive. In another preferred variant, x ranges from 0 to 150, inclusive, y ranges from 0 to 150, inclusive, and the sum of x and y is from 75 to 300, inclusive; more preferably, the sum of x and y is from 100 to 300, inclusive.

One particularly preferred ester of alkoxylated benzyl alcohol is PPG-3 benzyl myristate, in which x is 0, y is 3, and $R^{13}$ contains 13 carbon atoms:

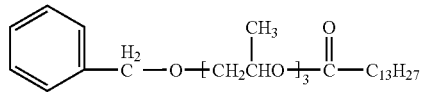

PPG-3 benzyl myristate.

Another particularly preferred ester of alkoxylated benzyl alcohol is PPG-10 benzyl propionate, in which x is 0, y is 10, and $R^{13}$ has 3 carbon atoms:

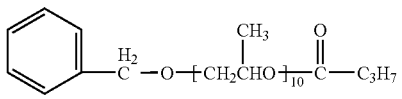

PPG-10 benzyl propionate.

Other non-limiting examples of the esters of alkoxylated benzyl alcohol are:

PEG-3, PPG-10 benzyl behenate

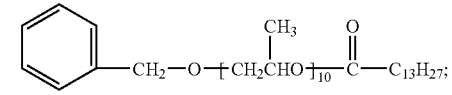

PPG-10 benzyl myristate

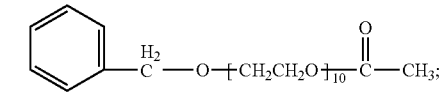

PEG-10 benzyl acetate

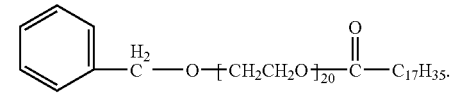

PEG-20 benzyl stearate

The esters of the formula (II)

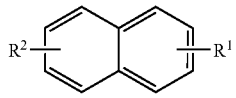

(II)

are derivatives of alkoxylated aromatic alcohols containing a naphthalene nucleus. In the preferred esters of the formula (II), $R^1$ is

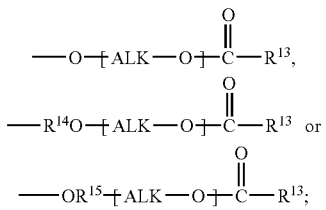

and $R^2$ is hydrogen,

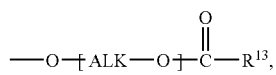

—O—[ALK—O]—H,

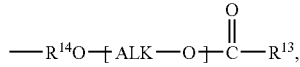

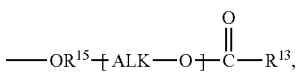

—R$^{14}$O–[ALK—O]–H  or  —OR$^{15}$–[ALK—O]–H.

For disubstituted esters of the formula (II), the preferred positional isomers are:

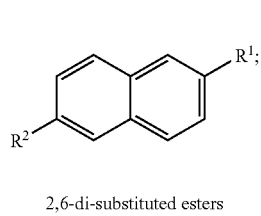

2,6-di-substituted esters

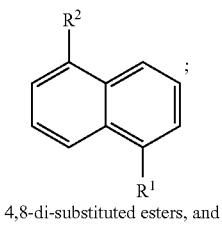

4,8-di-substituted esters, and

The mono-substituted esters of the formula (II), where R$^2$ is hydrogen are more preferred. The 2-substituted esters of the formula (II) are especially preferred:

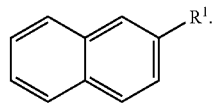

Non-limiting examples of the esters of the formula (II) are

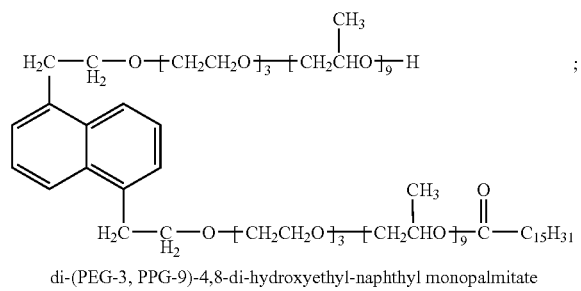

di-(PEG-3, PPG-9)-4,8-di-hydroxyethyl-naphthyl monopalmitate

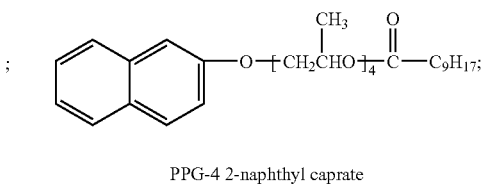

PPG-4 2-naphthyl caprate

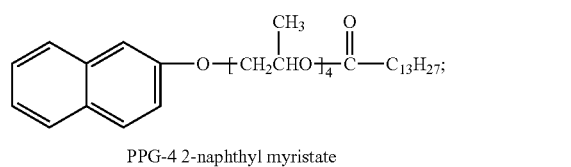

PPG-4 2-naphthyl myristate

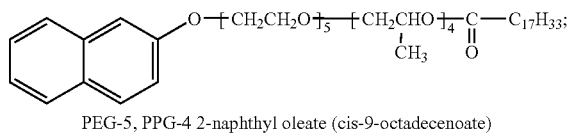

PEG-5, PPG-4 2-naphthyl oleate (cis-9-octadecenoate)

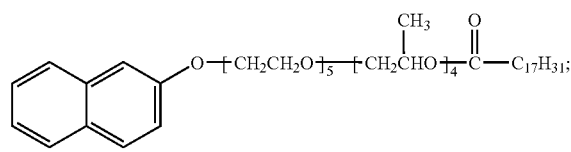

PEG-5, PPG-4 2-naphthyl linoleate (cis, cis-9,12-octadecadienoate)

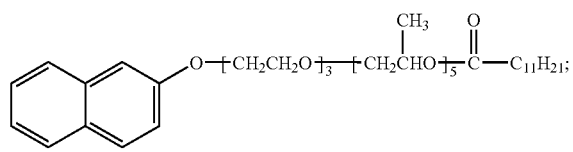

PEG-3, PPG-5 2-naphthyl laurate

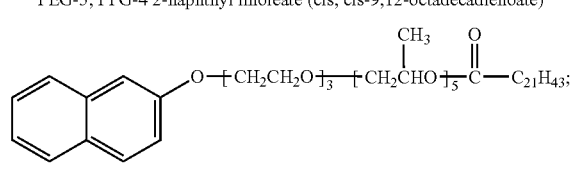

PEG-3, PPG-5 2-naphthyl behenate

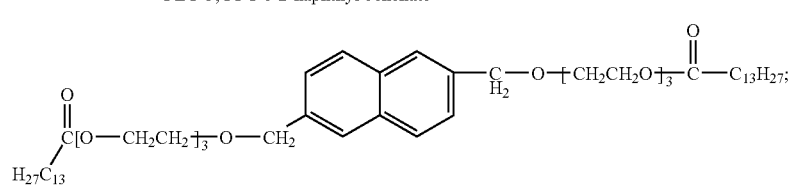

di-(PEG-3)-2,6-di-hydroxymethyl-naphthyl dimyristate

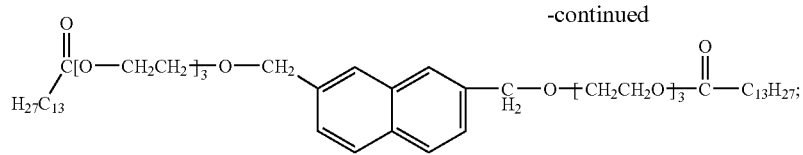

di-(PEG-3)-2,7-di-hydroxymethyl-naphthyl dimyristate and

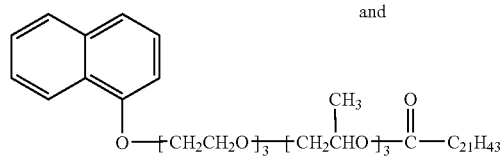

PEG-3, PPG-5 4-naphthyl behenate.

The esters of the formul (III)

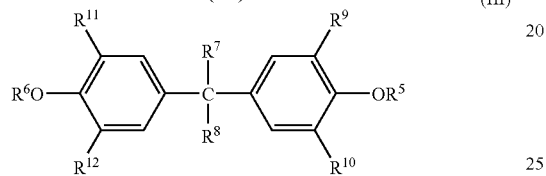

(III)

are derivatives of various bisphenol-type compounds having two or more benzene nuclei. In the preferred esters of the formula (III), $R^5$ is as defined above, $R^6$ is $\pm[ALK{-}O\pm]H$ or

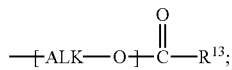

$R^7$ is hydrogen, methyl or trifluoromethyl; $R^8$ is hydrogen, methyl, trifluoromethyl, —CHCl$_2$ or

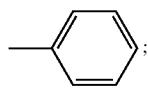

and $R^9$, $R^{10}$, $R^{11}$, and $R^{12}$ are independently hydrogen or methyl.

Preferred groups of the esters of the formula (III) include the derivatives of

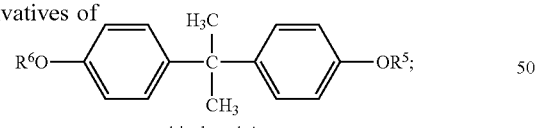

bisphenol A

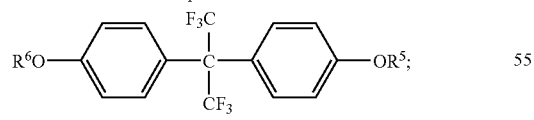

bisphenol AF

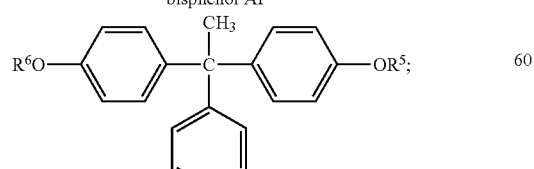

bisphenol AP

Non-limiting examples of the esters of the formula (III) are:

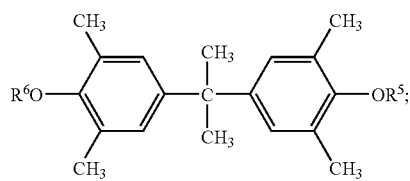

tetramethyl bisphenol A

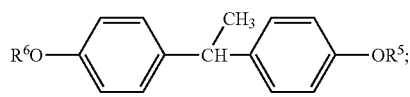

bisphenol E

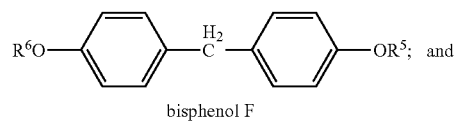

bisphenol F; and

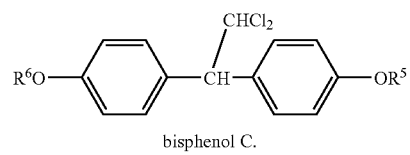

bisphenol C.

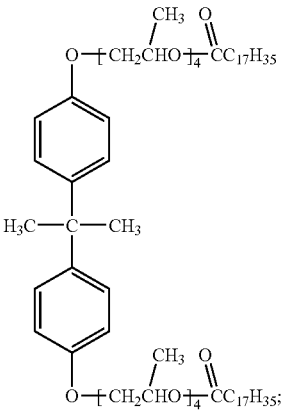

di-(PPG-4) Bisphenol A distearate

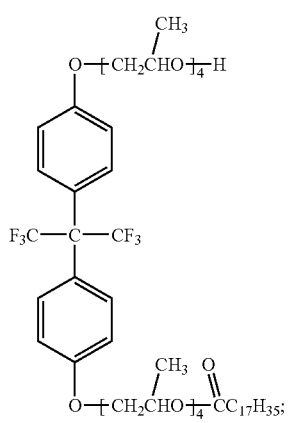
di-(PPG-4) Bisphenol AF monostearate
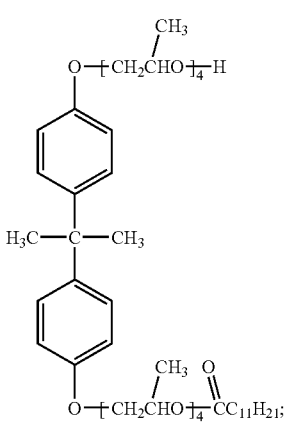
di-(PPG-4) Bisphenol A monolaurate
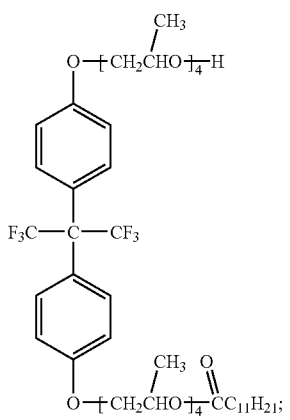
di-(PPG-4) Bisphenol AF Monolaurate
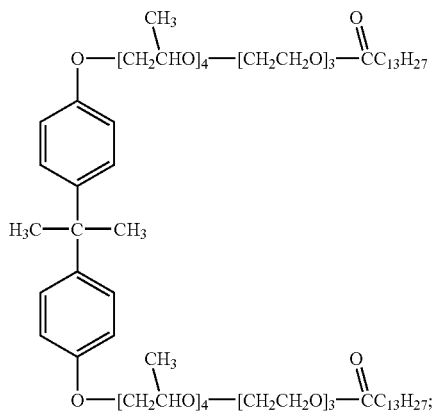
di-(PEG-3, PPG-4) Bisphenol A dioleate
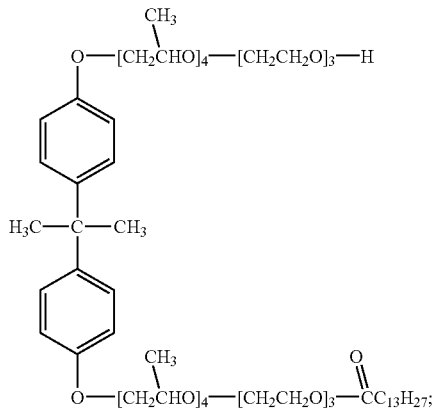
di-(PEG-3, PPG-4) Bisphenol A monomyristate
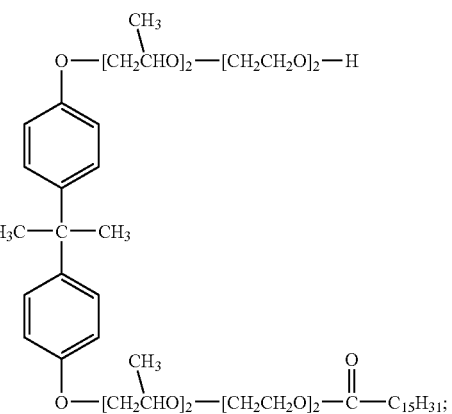
di-(PEG-2, PPG-2) Bisphenol A monopalmitate

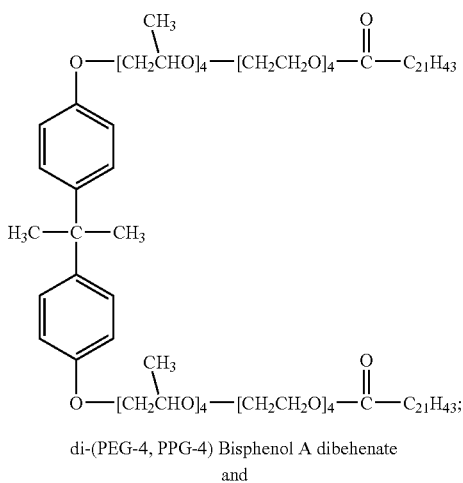

di-(PEG-4, PPG-4) Bisphenol A dibehenate
and

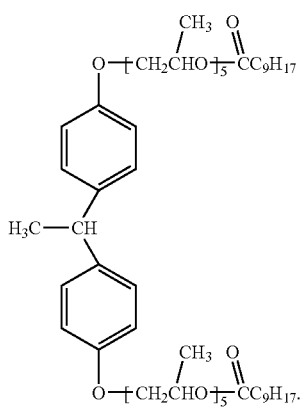

di-(PPG-5) Bisphenol E dicaprate.

The esters of the invention may be prepared in a variety of ways. The preferred esters of alkoxylated aromatic alcohol and fatty carboxylic acid are products of the reaction:

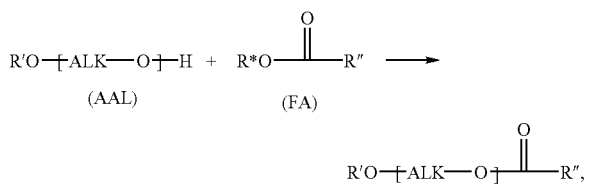

where R', R" and $-[ALK-O]-$ are defined above in reference to the product esters, and R* is hydrogen, lower alkyl group, or a carboxylate group. Thus, AAL is an aromatic alkoxylated alcohol and FA is a fatty carboxylic acid, a derivative of a fatty carboxylic acid, such as an ester or an anhydride, or mixtures thereof. Natural oils, synthetic oils and triglycerides that contain fatty carboxylic groups may also be used as the reactant FA.

Non-limiting examples of suitable fatty carboxylic acids include myristic acid, propionic acid, capric acid, lauric acid, behenic acid, erucic acid, linoleic acid, montan acid, phenyl acetic acid, oleic acid, stearic acid, palmitic acid, coconut-oil-derived acid mixture, palm oil-derived acid mixture, and mixtures thereof.

Non-limiting examples of suitable alkoxylated alcohols include alkoxylated benzyl alcohol, alkoxylated phenoxyethanol, alkoxylated cynnamyl alcohol, alkoxylated phenoxy-n-propanol, alkoxylated phenoxy-i-propanol, and mixtures thereof. Other non-limiting examples of suitable alkoxylated alcohols include alkoxylated bisphenol A, alkoxylated bisphenol AF, alkoxylated bisphenol AP, alkoxylated tetramethyl bisphenol A, alkoxylated bisphenol F, alkoxylated bisphenol E, alkoxylated bisphenol C, alkoxylated bisphenol M, alkoxylated bisphenol P, alkoxylated bisphenol S, alkoxylated bisphenol Z and mixtures thereof.

The synthesis of an alkoxylated aromatic alcohol (AAL) typically involves alkoxylation of the corresponding aromatic alcohol. The reaction schemes below illustrate the alkoxylation reaction, showing the ethoxylation/propoxylation of benzyl alcohol:

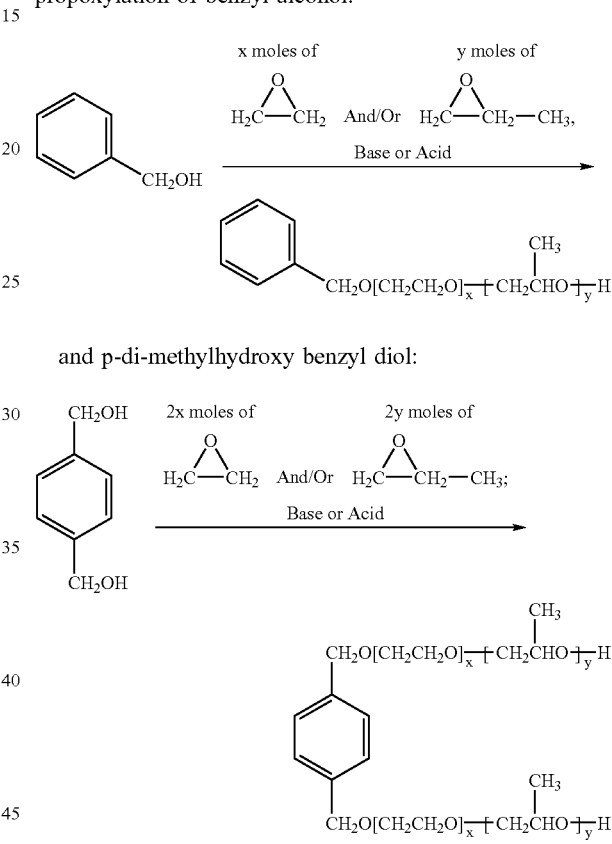

and p-di-methylhydroxy benzyl diol:

Preferably, the alkoxylation is carried out with ethylene oxide, propylene oxide or mixtures of ethylene oxide and propylene oxide. The alkoxylation of mono-hydroxy aromatic alcohols (e.g., benzyl alcohol, cynnamyl alcohol, phenoxyethanol, etc.) provides alkoxylated aromatic alcohols having a single hydroxy group at the end of the alkoxy chain. The alkoxylation of di-hydroxy aromatic alcohols typically provides alkoxylated aromatic alcohols having two hydroxy groups at the end of each alkoxy chain.

The alkoxylation reaction may produce symmetrical or asymmetrical alkoxylated alcohols. The order of the addition of the alkyl oxides (e.g., ethyl oxide and propyl oxide) may be used to vary the nature of the alkoxy substitution in the final esters, including the structural order of ethoxy and propoxy units, and the order of attachment. For example, alkyl oxides may be added sequentially, in a mixture, or in any other desired manner, thus varying the order of the alkoxy substitution. The amounts of alkyl oxide(s) introduced in the reaction zone and the duration of the reaction with the selected alkyl oxide(s) determines the number of moles of the alkyl oxide added to the starting aromatic alcohol. The numbers of ethoxy and propoxy units in the ester effects its properties. Thus, an increase in the amount of ethoxylation may be used to improve the solubility/dispersability of the ester while an increase in the amount of propoxylation improves fluidity.

The alkoxylation reaction may proceed via acidic or basic catalysis in the presence of such catalysts as alkali hydroxides and oxides, protic and Lewis acids, amines, quaternary ammonium compounds, water, and catalysts mixtures. The specific suitable catalysts include, for example, potassium hydroxide, sodium methoxide, sodium borohydride, boron trifluoride, stannic chloride, and sulfuric acid. The preferred catalysts are potassium or sodium hydroxide, sodium methoxide, sodium borohydride or mixtures thereof.

Preferably, the catalyst is used in the amount of from about 0.1 to about 2.0 weight percent of the weight of the desired alkoxylated alcohol. Preferably, the reaction is carried out under anhydrous conditions at from about 110° C. to about 200° C. at pressures of from about 10 psig to about 80 psig. Higher temperatures and pressures may be also utilized. After the reaction is complete, an acid (e.g., phosphoric or acetic acid) may be introduced to neutralize the catalyst.

The alkoxylated aromatic alcohols produced in the alkoxylation reaction are then esterified, providing the esters of alkoxylated aromatic alcohols and fatty carboxylic acid of the invention. The esterification reaction may be carried out in a conventional manner. Typically, the stoichiometric quantities of the alcohol and the fatty acid are combined in the presence of a suitable catalyst. A slight stoichiometric excess of one of the reagents may be employed. The preferred catalysts include methanesulfonic acid and para-toluenesulfonic acid.

Generally, the aromatic alkoxylated alcohol, the acid and the catalyst are combined with mixing to form a reaction mixture. The reaction mixture is heated with mixing at a temperature between about 155° C. and about 250° C., preferably between about 170° C. and 220° C., until an acid value of less than 8 mg KOH, preferably less than 5 mg KOH, is obtained. The reaction mixture is cooled below 85° C. and washed with water. The ester layer is separated and heated under vacuum until moisture content of less than 0.2 percent is obtained.

The esterification of alkoxylated aromatic alcohols having a single hydroxy group is straightforward. If a stoichiometric excess of the fatty acid or the derivative of fatty acid is provided, the alkoxylated aromatic alcohol is entirely consumed in the reaction, providing a monoester of alkoxylated aromatic alcohol and the fatty acid. The reaction scheme below illustrates the esterification of PEG-4, PPG-4 benzyl ether by myristic acid, providing 4-PEG-4-PPG benzyl myristate:

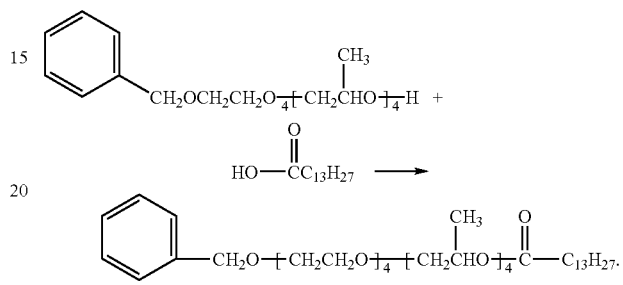

The esterification of the alkoxylated aromatic alcohols having two or more hydroxy groups capable of being esterified may result in monoesters, diesters and so on. The nature of the esterification product depends on the relative proportions of the fatty carboxylic acid (or the derivative thereof) and the alkoxylated aromatic alcohol. For example, the esterification of alkoxylated aromatic alcohols having two hydroxy groups may result in one or both of the hydroxy groups being esterified, as desired. If a stoichiometric excess of the alkoxylated aromatic alcohol is present in the reaction mixture, the monoester is the predominant product. Conversely, if a stoichiometric excess of the fatty acid is used, the predominant product is the diester.

The reaction scheme below illustrates the esterification of PEG-4, PPG-4 p-di-methylhydroxy benzyl ether by myristic acid, providing either di- or mono-myristate depending on the relative proportions of the reactants:

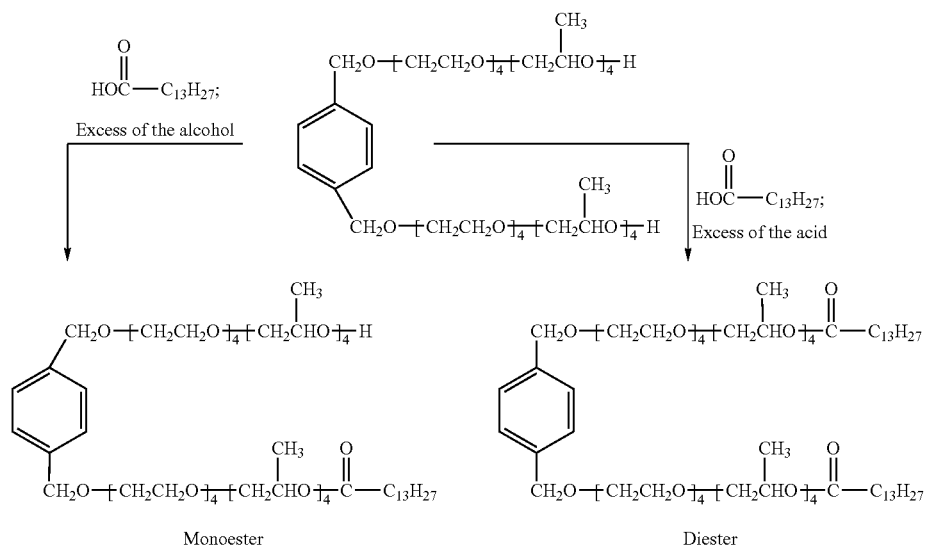

The descriptions of the preparation methodologies, including the alkoxylation and esterification reactions, in U.S. Pat. Nos. 5,693,316, 5,597,555, 5,455,025, and 5,302,377 are incorporated herein by reference to the extent such descriptions are relevant to the preparation of the esters of the invention.

The esters of alkoxylated aromatic alcohols and fatty carboxylic acids are useful as ingredients or additives for cosmetic and personal care products. Preferably, the esters described herein are utilized as emollients, solubilizers, diluents, plastisizers, and/or thickeners. As ingredients of personal care and cosmetic products, the esters of alkoxylated aromatic alcohols and fatty carboxylic acids may provide one or more important advantages to the formulator. First of all, the formulations containing the esters of the invention have a non-greasy skin feel desirable for cosmetic and personal care products. This, of course, depends on other ingredients of the formulation.

Further, it has been surprisingly found that the solubility of certain functional ingredients of cosmetic products in certain esters of alkoxylated aromatic alcohols and fatty carboxylic acids is greater than the solubility of the identical active ingredients in the conventionally used emollients. For example, the solubility of benzophenone-3, a known sunscreen active ingredient for sunscreen product formulations, in PPG-3 benzyl myristate is greater than the solubility of benzophenone-3 in the mixture of benzoic acid esters of $C_{12}$, $C_{13}$, $C_{14}$, and $C_{15}$ linear primary alcohols, which is a known emollient ingredient described in U.S. Pat. No. 4,323,694, which is incorporated herein by reference. The esters of alkoxylated aromatic alcohols and fatty carboxylic acids that dissolve an amount of benzophnone-3 which is 10% or greater than the amount dissolved in the equal quantity of the emollient ingredient described in the '694 patent are preferred.

It is another advantage that the synthetic methodology for preparation of the esters of the invention provides ability to modify the properties of the cosmetic and personal care product containing the esters. For example, by modifying the ratios of ethoxy and propoxy groups in the alkoxy spacer, the fluidity and/or dispersability of the esters in surfactant systems may be varied as the formulator desires. To impart additional fluidity, the propoxy units are included in the alkoxy spacer of the ester. Conversely, the ethoxy units may be included to improve the solubility/dispersability of the esters.

Compounds that impart the products with low spreading properties allow formation of thicker, more uniform films. Such compounds are desirable for obtaining, for example, sunscreen formulations with a high resistance to wash off and a high SPF value. Therefore, the esters of alkoxylated aromatic alcohols and fatty carboxylic acids having a skin spread factor of less than 10 or a viscosity of less then 20,000 cps are preferred. The more preferred esters have a skin spread factor of less than 5 or a viscosity of less then 10,000 cps. The esters that exhibit both low spread factor and viscosity are yet more preferred.

The skin spread factor is determined by applying, for example, 5 microliters of a product to a 3.14 cm diameter circle on the volar surface of the forearm. The product is spread evenly within the circle and allowed to spread for a fifteen minute period. The test site and surrounding area of the forearm is then sprayed with a 1 percent solution of FD&C Blue No. 1. The area not stained by the blue dye indicates the area onto which the product spread. The skin-spread factor is obtained by dividing the resulting area by the initial area. In accordance with the present invention, the test formulations containing the esters of the invention preferably have a skin spread factor of less than about 10, more preferably less than about 5.

Desirable pigment wetting properties may also be obtained by using the esters of the invention. Pigment wetting properties are determined by preparing a dye slurry and measuring viscosity. For example, a slurry can be prepared using an alkoxylated fatty alcohol dicarboxylic acid ester of the present invention mixed with 35 percent mica or any dye. The viscosity of the slurry is determined after allowing the slurry to stand for five minutes. The lower the viscosity, the better the pigment wetting properties of the ester. Preferably, in accordance with the present invention, viscosity of the resulting dye slurry will be below about 20,000 cps, more preferably, less than about 10,000 cps; based on a 65% ester, 35% pigment mixture (measured in weight percent). Viscosity will vary if a different testing mixture is used.

Thus, the invention may provide personal care or cosmetic product compositions that include the esters of alkoxylated aromatic alcohols and fatty carboxylic acids described herein. Such compositions are referred to herein as the final product compositions. The final product compositions of the invention contain from about 0.1% to about 99% of at least one ester of alkoxylated aromatic alcohol and fatty carboxylic acid by weight of the composition. The amount of the ester(s) in the product composition depends on the specific application and formulation design. Preferably, the esters of the invention are present in the amount from about 0.1% to about 40%, more preferably, from about 0.1% to about 10%, yet more preferably, from about 0.5% to about 2% by the weight of the product composition. However, different amounts may be preferred depending on the nature of the product.

In addition to the esters of alkoxylated aromatic alcohols and fatty carboxylic acids, the final product compositions of the invention may include various functional ingredients, including active and additional ingredients, both conventional and otherwise. The decision to include or exclude an ingredient and the selection of specific active and additional ingredients depends on the specific application and product formulation. The line of demarcation between an "active" ingredient and an "additional ingredient" is artificial and dependent on the specific application and product type. A substance that is an "active" ingredient in one application or product may be an "additional" ingredient in another, and vice versa.

Thus, in addition to the esters of alkoxylated aromatic alcohols and fatty carboxylic acids, the final product compositions of the invention may include one or more active ingredients present in the amount from 0.2% to about 60%, preferably, from about 3% to about 40%, more preferably, from about 5% to 25% by weight of the composition. The active ingredients provide some benefit related to the function of the product. Non-limiting examples of the active ingredients include sunscreen compounds, both organic and inorganic, pigments, skin and hair rejuvenating agents, such as bioactives, moisturizers, film formers, hair colors, make-up agents, detergents, thickening agents, emulsifiers, antiseptic agents, deodorant actives and surfactants cleaning agents, hair conditioning agents, skin conditioning agents, hair styling agents, antidandruff agents, hair growth promoters, perfumes, antiseptic agents, surfactants and pharmaceuticals useful for topical purposes for transdermal delivery. Other suitable active ingredients and the specific types of the active ingredients can be found in the general ingredients section herein.

For each type of active ingredient, one or more compounds may be present. Likewise, more than one type of active ingredient may be present in the product composition. The choice of the active ingredient depends on the nature of the desired cosmetic or personal care product. For example, the sunscreens may be used in the sunscreen lotions, shampoos, hair care lotions and the like. The choice of the active ingredient(s) depends on the nature of the desired cosmetic or personal care product. For example, the sunscreen actives may be used in the sunscreen lotions, shampoos, medicated shampoos, hair care lotions and the like.

In addition to esters of alkoxylated aromatic alcohols and fatty carboxylic acid and the active ingredient(s), the compositions of the invention may include one or more additional emollients, detergents, emulsifiers, humectants, antioxidants, softeners, lubricants, penetrants, plastisizers, solvents and co-solvents, sunscreening additives, dispersants, anti-perspirants, conditioners, thickening agents, preservatives, antimicrobial agents, buffers, chelating agents, foaming agents, coupling agents, proteins, salts, essential oils and fragrances.

The final product compositions of the invention may be in the form of liquids, gels, creams, emulsions, aerosol and non-aerosol sprays, microemulsions, foams, and solids, and may be clear or opaque. The clear preparations are preferred. The final product compositions of the invention, including those in the form of products described herein, may be used for both skin and hair. The final product compositions of the invention may also have the form of household cleaning products, household detergent liquids and other similar products.

The final product compositions of the invention may be formulated as aqueous and non-aqueous preparations, including but not limited to topical preparations. In addition to the esters of alkoxylated aromatic alcohols and fatty carboxylic acids, the topical preparations of the invention may contain various active, additional and optional ingredients described in the ingredients section herein. For example, additional emollient agents, such as mineral oil, petrolatum, fragrances, proteins, humectants, salts, preservatives, essential oils and the like may be included in the topical preparations of the invention.

The aqueous topical preparations of the invention contain the esters of alkoxylated aromatic alcohols and fatty carboxylic acids the invention in the amount of from about 0.20 to about 60.0 percent, preferably from about 3.0 to about 40.0 percent, more preferably, 5 to 25 percent by weight of the composition, and one or more active ingredients in the amount from about 0.20 to about 60.0 percent, preferably from about 3.0 to about 40.0, more preferably, 5 to 30 percent by weight of the composition. If additional conventional emollients are used in the composition, they may be present in a ratio of from about 10:1 to about 1:10 parts to the ester compounds of the invention. The balance is generally excipients and water or some aqueous solvent system.

The non-aqueous topical preparations of the invention contain the esters of alkoxylated aromatic alcohols and fatty carboxylic acids in the amount of from about 0.10 to about 99.0 percent, preferably from about 10 to about 90.0 percent, and more preferably from about 15 to about 75 percent by weight of the composition, and one or more of the active ingredients in the amount from about 0.20 to about 99.0 percent, preferably, from about 10 to about 90.0 percent, and more preferably, from about 15 to about 75 percent by weight of the composition. If additional conventional emollients are used in the composition, they may be included in a ratio of from about 10:1 to about 1:10 to the ester(s) of the invention.

Non-limiting examples of the final product compositions of the invention include sunscreen compositions for hair and/or skin, such as lotions, gels, sprays, and the like, hand cleaners, bath compositions, bubble-bath products, suntan oils, anti-perspirant and/or deodorant compositions, perfumes and colognes, cold creams, shaving products and pre-shaves, deodorants, topical pharmaceutical ointments, skin moisturizers, facial cleansers, cleansing creams, skin gels, shampoos, hair conditioners, detergents, household cleaning products, non-woven toilettes, make-up products, lipstick products, mascara, and hair coloring products.

The esters of the invention are especially suitable for use in certain cosmetic and personal care products. The preferred products include shampoos, hair conditioners, sunscreen product formulations, antiperspirants, baby shampoos, baby bath products, hand dishwashing liquids, body washes, facial washes, and baby wipes.

The particularly preferred final product compositions of the invention are antiperspirant products and sunscreen product formulations. Such more preferred compositions are preferably topically applied to skin or hair. The esters of the invention are highly compatible with silicon liquids, such as cyclomethicone compounds. Cyclomethicones are volatile compounds, which are often included in the antiperspirant products. However, the volatility of the cyclomethicones, which is desired in the antiperspirant products, makes them difficult to handle during formulation processing. It has been surprisingly discovered that certain esters of alkoxylated aromatic alcohols and fatty carboxylic acids reduce the volatility of cyclomethicones in processing without substantially affecting their performance in the antiperspirant products. Thus, the invention also provides antiperspirant product compositions that include the esters of alkoxylated aromatic alcohols and fatty carboxylic acids present in the amount of from about 0.1% to about 40%, more preferably, from about 1% to about 20% by weight of the composition, one or more antiperspirant actives present in the amount of from about 1% to about 20%, more preferably, from about 5% to about 15% by weight of the composition, and one or more cyclomethicone compounds present in the amount of from about 1% to about 40%, more preferably, from about 2% to about 20% by weight of the composition. A raw material blend of the esters of the invention and at least one cyclomethicone compound is also contemplated. Such blend preferably contains from about 20% to about 80% of the ester and from about 20% to about 80% of at least one cyclomethicone compound. The antiperspirants product compositions containing the esters of alkoxylated aromatic alcohols and fatty carboxylic acids may also contain a variety of other ingredients, including those traditionally included. Non-limiting examples of such ingredients are aluminum zirconium complexes, such as aluminum zirconium tetrachlorohydrex-glycine; aluminum chlorohydrates; sodium aluminum chlorohydroxy lactate; aluminum chlorohydrex P.G.; glycols, such as dipropylene glycol, hexalene glycol and the like; silicones, such as phenyl trimethicone; talc and the like; hydroxyethyl cellulose and the like; PEG distearate and the like; fatty esters, such as isopropyl myristate and the like; alkoxylated alcohols, such as isoceteth-20 and the like; ethanol; polydecene and the like; polyethylene; silica; fatty alcohols, such as cetyl, stearyl and cetearyl; hydrogenated vegetable oils, such as hydrogenated castor oil and the like; glyceryl behenate; $C_{18-36}$ acid triglycerides; and $C_{18-36}$ acid glycol esters. Other suitable specific ingredients are described herein in the general ingredients section.

The esters of the invention are also especially useful as ingredients of sunscreen product formulations, such as sunscreen lotions, sunscreen lotion sprays, UV-protecting shampoos and conditioners, cosmetic formulations having a sun-protection function, and the like. Thus, the invention also provides sunscreen product compositions that include the esters of the invention present in the amount of from about 0.5% to about 60%, more preferably, from about 1% to about 40% by weight of the composition, and one or more sunscreen active ingredients present in the amount of from about 0.1% to 30%, more preferably, from about 1% to about 20% by weight of the composition. Non-limiting examples of the sunscreen active ingredients that may be used in the sunscreen product formulations of the invention include p-amino benzoates, salicylates, ferrulic acid derivatives, phenylbenzimidazole sulfonic acids, benzophenone sulfonic acids, benzophenones, thioctic acids derivatives, oil-soluble cinnamates, and the like. The sunscreen active ingredients present in the sunscreen products of the invention include nonionic, cationic and anionic UV-absorbing compounds, such as benzophenone-3, octyl methoxycinnamate, phenylbenzimidazole sulfonic acid, menthyl anthranilate, cinnamidopropyl trimonium chloride and the like. Other specific non-limiting examples of the sunscreen active ingredients include para-aminobenzoic acid, benzophenone-1, benzophenone-1, benzophenone-2, benzophenone-4, benzophenone-5, benzophenone-6, benzophenone-8, benzophenone-12, methoxycinnamate, avobenzone, ethyl dihydroxypropyl para-aminobenzoate, glyceryl para-aminobenzoate, methyl anthranilate, octocrylene, octyl dimethyl para-aminobenzoate, octyl salicylate, zinc oxide, titanium dioxide, and red petrolatum. In one preferred embodiment, the esters of the formula (II) are used in combination with avobenzone.

The sunscreen product compositions containing the esters of alkoxylated aromatic alcohols and fatty carboxylic acids may also contain a variety of other ingredients, including those traditionally included. Non-limiting examples of such ingredients, which may be present in the sunscreen product compositions of the invention, are mineral oil; fatty acid esters, such as octyl palmitate and the like; emulsifiers, such as oleth-10, PEG-10 cetyl alcohol and the like; non-alkoxylated alcohol phosphate esters, such as cetyl phosphate or dicetyl phosphate; alkoxylated alcohol phosphate esters, such as PEG-10 cetyl phosphate and the like; polymeric emulsifiers, such as carbomer-type and the like; physical blockers, such as zinc oxide and titanium dioxide; fatty alcohols, such as cetyl, stearyl and cetearyl; vitamins, such as vitamin E, C and the like; antioxidants, such as BHT, BHA, and the like. Other suitable specific ingredients are described herein in the general ingredients section.

The shampoos containing the esters of alkoxylated aromatic alcohols and fatty carboxylic acids may include a variety of ingredients, including those traditionally included. Non-limiting examples of such ingredients are ammonium lauryl sulfate, ammonium laureth sulfate, sodium lauryl sulfate, and sodium laureth sulfate; amphoteric surfactants (e.g., cocoamphoglycinate, cocoamidopropyl betaine and the like); amine oxides, such as cocoamine oxide and the like; cellulose and cationic cellulose, for example, polyquat 10; guar gum and cationic guar gum; UV-absorbing compounds, such as benzophenone-3, phenylbenzimidazole sulfonic acid, menthyl anthranilate, cinnamidopropyl trimonium chloride, and octylmethoxycinnamate; silicone fluids (cyclomethicone) and modified silicone fluids (amodimethicone); botanical extracts; and fatty esters and triglycerides, such as octyl stearate and wheat germ oil. Other suitable specific ingredients are described herein in the general ingredients section.

The baby shampoos and baby baths containing the esters of alkoxylated aromatic alcohols and fatty carboxylic acids may contain a variety of ingredients, including those traditionally included. Non-limiting examples of such ingredients are ammonium lauryl sulfate, ammonium laureth sulfate, sodium lauryl sulfate, and sodium laureth sulfate; amphoteric surfactants, such as cocoamphoglycinate, cocoamidopropyl betaine and the like; amine oxides, such as cocoamine oxide and the like; cellulose and cationic cellulose like polyquat 10; guar gum and cationic guar gum; UV-absorbing compounds, such as benzophenone-3 and octylmethoxycinnamate; silicone fluids (cyclomethicone) and modified silicone fluids (amodimethicone); botanical extracts; fatty esters and triglycerides, such as octyl stearate and wheat germ oil; alkoxylated glycerides, such as PEG-30 glyceryl cocoate; alkoxylated sorbitan esters, such as polysorbate 20; and carboxylated surfactants, such as trideceth-10 carboxylate. Other suitable specific ingredients are described herein in the general ingredients section.

The body and facial washes containing the esters of alkoxylated aromatic alcohols and fatty carboxylic acids may include a variety of ingredients, including those traditionally included. Non-limiting examples of such ingredients are ammonium lauryl sulfate, ammonium laureth sulfate, sodium lauryl sulfate, and sodium laureth sulfate; amphoteric surfactants, such as cocoamphoglycinate, cocoamidopropyl betaine and the like; amine oxides, such as cocoamine oxide and the like; cellulose and cationic cellulose, such as polyquat 10; guar gum and cationic guar gum; UV-absorbing compounds, such as benzophenone-3 and octylmethoxycinnamate; silicone fluids (cyclomethicone) and modified silicone fluids (amodimethicone); botanical extracts; fatty esters and triglycerides, such as octyl stearate and wheat germ oil; alkoxylated glycerides, such as PEG-30 glyceryl cocoate; alkoxylated sorbitan esters, such as polysorbate 20; carboxylated surfactants, such as trideceth-10 carboxylate; lanolin and lanolin quats; and petrolatum. Other suitable specific ingredients are described herein in the general ingredients section.

The hair conditioners containing the esters of alkoxylated aromatic alcohols and fatty carboxylic acids may also contain a variety of other ingredients, including those traditionally included. Non-limiting examples of such ingredients are fatty quats, such as behentrimonium chloride; fatty alcohols, such as cetyl alcohol; cellulose and cationic cellulose, such as polyquat 10; guar gum and cationic guar gum; nonionic, cationic and anionic UV-absorbing compounds, such as benzophenone-3, octyl methoxycinnamate, phenylbenzimidazole sulfonic acid, menthyl anthranilate, cinnamidopropyl trimonium chloride and the like; silicone fluids (cyclomethicone) and modified silicone fluids (amodimethicone); botanical extracts; fatty esters and triglycerides, such as octyl stearate and wheat germ oil; fatty alkyl phosphate esters, such as dicetyl phosphate and PEG-20 cetyl phosphate; alkoxylated sorbitan esters, such as polysorbate 20; and carboxylated surfactants, such as trideceth-10 carboxylate. Other suitable specific ingredients are described herein in the general ingredients section.

The hand dish wash liquids containing the esters of alkoxylated aromatic alcohols and fatty carboxylic acids may also contain a variety of other ingredients, including those traditionally included. Non-limiting examples of such ingredients are ammonium lauryl sulfate, ammonium laureth sulfate, sodium lauryl sulfate, and sodium laureth sulfate; sodium and magnesium salts of dodecyl benzene sulfonate; alkanolamides, such as cocamide DEA or cocamide MEA;

amphoteric surfactants, such as cocoamphoglycinate, cocoamidopropyl betaine and the like; and amine oxides, such as cocoamine oxide and the like.

The baby wipes containing the esters of alkoxylated aromatic alcohols and fatty carboxylic acids may also contain a variety of other ingredients, including those traditionally included. Non-limiting examples of such ingredients are ammonium lauryl sulfate, ammonium laureth sulfate, sodium lauryl sulfate, and sodium laureth sulfate; amphoteric surfactants, such as cocoamphoglycinate, cocoamidopropyl betaine and the like; amine oxides, such as cocoamine oxide and the like; cellulose and cationic cellulose, such as polyquat 10; guar gum and cationic guar gum; UV-absorbing compounds, such as benzophenone 3 and octylmethoxycinnamate; silicone fluids (cyclomethicone) and modified silicone fluids (amodimethicone); botanical extracts; fatty esters and triglycerides, such as octyl stearate and wheat germ oil; alkoxylated glycerides, such as PEG-30 glyceryl cocoate; PEG-75 lanolin; alkoxylated sorbitan esters, such as polysorbate 20; carboxylated surfactants, such as trideceth-10 carboxylate; non-alkoxylated alcohol phosphate esters, such as cetyl phosphate or dicetyl phosphate; alkoxylated alcohol phosphate esters, such as PEG-10 cetyl phosphate and the like. Other suitable specific ingredients are described herein in the general ingredients section.

The following ingredients also may be present in the compositions of the invention.

Surfactants

Various surfactants may be present in the compositions of the invention, including one or more nonionic surfactants, anionic surfactants, cationic surfactants, amphoteric surfactants, zwitterionic surfactants, and mixtures thereof. For some of surfactants that may be used in combination with the compositions of the invention, please see McCutcheon's, Detergents and Emulsifiers, (1986), U.S. Pat. Nos. 5,151,210, 5,151,209, 5,120,532, 5,011,681, 4,788,006, 4,741,855, U.S. Pat. Nos. 4,704,272, 4,557,853, 4,421,769, 3,755,560; all incorporated herein by reference in their entirety.

Cationic Surfactants

Various cationic surfactants may be present in the compositions of the invention. The amounts and the nature of cationic surfactants present in the compositions of the invention depend on the nature of the composition. In the final product composition, the total amount of cationic surfactants, including the alkoxylated esters thereof described herein, may vary from 0.1% to about 40%, more preferably, from about 0.1% to about 15%, yet more preferably, from about 0.5% to about 2% by the weight of the product composition. However, different amounts of cationic surfactants may be preferred depending on the nature of the product. Suitable additional cationic surfactants are disclosed in McCutcheon, Detergents & Emulsifiers, (M.C. Publishing Co. 1979); U.S. Pat. Nos. 3,155,591, 3,929,678, 3,959,461, 4,387,090, which are incorporated by reference herein.

Ammonium Quats

The compositions of the invention may include quaternary ammonium cationic surfactants of the formula

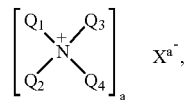

where X and a are as previously described, $Q_1$ is $C_{12}$–$C_{22}$ alkyl, $C_{12}$–$C_{22}$ alkyl amido $C_1$–$C_6$ alkylene, $C_{12}$–$C_{22}$ alkylhydroxy; $Q_2$ is $C_{12}$–$C_{22}$ alkyl, $C_{12}$–$C_{22}$ alkyl amido $C_1$–$C_6$ alkylene, $C_{12}$–$C_{22}$ alkylhydroxy, benzyl, or $C_1$–$C_6$ alkyl; $Q_3$ and $Q_4$ are independently $C_1$–$C_6$ alkyl or benzyl.

Examples of suitable quaternary ammonium surfactants include cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof.

Additional quaternary ammonium salts include those wherein the $C_{12}$–$C_{22}$ alkyl is derived from a tallow fatty acid or from a coconut fatty acid. Examples of quaternary ammonium salts derived from these tallow and cococut sources include ditallow dimethyl ammonium chlroide, ditallow dimehtyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

More preferred quaternary ammonium surfactants are dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Fatty Amines

The compositions of the invention may also include salts of primary, secondary and tertiary $C_{12}$–$C_{22}$ amines. Examples of such suitable amines include stearamido propyl dimethyl amine, diethyl amino ethyl stearamide, dimethyl stearamine, dimethyl soyamine, soyamine, tri(decyl)amine, ethyl stearylamine, ethoxylated stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Some cationic amine surfactants useful in the compositions of the present invention are disclosed in U.S. Pat. No. 4,275,055, incorporated by reference herein.

Amidoamines

The compositions of the invention may also include amidoamines, such as disclosed in U.S. patent application Ser. No. 09/409,203, assigned to Croda Inc., and incorporated by reference herein.

Non-ionic Surfactants

The compositions of the invention may also include various non-ionic surfactants. Among the suitable nonionic surfactants are condensation products of $C_8$–$C_{30}$ alcohols with sugar or starch polymers. These compounds can be represented by the formula $(S)_n$—O—R, wherein S is a sugar moiety such as glucose, fructose, mannose, and galactose; n is an integer of from about 1 to about 1000, and R is $C_8$–$C_{30}$ alkyl. Examples of suitable $C_8$–$C_{30}$ alcohols from which the R group may be derived include decyl alcohol, cetyl alcohol, stearyl alcohol, lauryl alcohol, myristyl alcohol, oleyl alcohol, and the like. Specific examples of these surfactants include decyl polyglucoside and lauryl polyglucoside.

Other suitable nonionic surfactants include the condensation products of alkylene oxides with fatty acids (i.e., alkylene oxide esters of fatty acids). These materials have the general formula $RCO(X)_n$ OH, wherein R is a $C_{10}$–$C_{30}$ alkyl, X is —$OCH_2CH_2$— (derived from ethylene oxide) or —$OCH_2CHCH_3$— (derived from propylene oxide), and n is an integer from about 1 to about 200.

Yet other suitable nonionic surfactants are the condensation products of alkylene oxides with fatty acids (i.e., alkylene oxide diesters of fatty acids) having the formula $RCO(X)_nOOCR$, wherein R is a $C_{10}$–$C_{30}$ alkyl, X is —$OCH_2CH_2$— (derived from ethylene oxide) or —$OCH_2CHCH_3$— (derived from propylene oxide), and n is an integer from about 1 to about 200.

Yet other nonionic surfactants are the condensation products of alkylene oxides with fatty alcohols (i.e., alkylene oxide ethers of fatty alcohols) having the general formula $R(X)_nOR'$, wherein R is $C_{10}$–$C_{30}$ alkyl, n is an integer from about 1 to about 200, and R' is H or a $C_{10}$–$C_{30}$ alkyl.

Still other nonionic surfactants are the compounds having the formula $RCO(X)_nOR'$ wherein R and R' are $C_{10}$–$C_{30}$ alkyl, X is —$OCH_2CH_2$— (derived from ethylene oxide) or —$OCH_2CHCH_3$— (derived from propylene oxide), and n is an integer from about 1 to about 200.

Examples of alkylene oxide-derived nonionic surfactants include ceteth-1, ceteth-2, ceteth-6, ceteth-10, ceteth-12, ceteraeth-2, ceteareth6, ceteareth-10, ceteareth-12, steareth-1, steareth-2, stearteth-6, steareth-10, steareth-12, PEG-2 stearate, PEG4 stearate, PEG6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amides disclosed, for example, in U.S. Pat. Nos. 2,965,576, 2,703,798, and 1,985,424, which are incorporated herein by reference.

Anionic Surfactants

The compositions of the invention may also include various anionic surfactants. Several examples of suitable anionic surfactants are disclosed in U.S. Pat. No. 3,929,678, which is incorporated herein by reference. Further examples of suitable anionic surfactants include alkoyl isethionates, and alkyl ether sulfates.

The alkoyl isethionates typically have the formula $RCO$——$OCH_2CH_2$—$SO_3M$, wherein R is $C_{10}$–$C_{30}$ alkyl, and M is a water-soluble cation, such as ammonium, sodium, potassium, or triethanolamine. The examples of suitable isethionates include ammonium cocoyl isethionate, sodium cocoyl isethionate, sodium lauroyl isethionate, sodium stearoyl isethionate, and mixtures thereof. Preferred for used herein are ammonium cocoyl isethionate, sodium cocoyl isethionate, and mixtures thereof.

The alkyl ether sulfates typically have the formulas $ROSO_3M$ and $RO(C_2H_4O)_xSO_3M$, where R is $C_{10}$–$C_{30}$ alkyl, x varies from about 1 to about 10, and M is a water-soluble cation such as ammonium, sodium, potassium and triethanolamine.

Yet another suitable class of anionic surfactants are alkali metal salts of $C_8$–$C_{30}$ carboxylic acids and alkylsulfonates of the formula $R_1$—$SO_3M$ (where $R_1$ is $C_8$–$C_{30}$ alkyl; preferably, $C_{12}$–$C_{22}$ alkyl, and M is a cation), including succinamates, and $C_{12}$–$C_{24}$ olefin sulfonates and carboxylates.

Amphoteric Surfactants

The compositions of the invention may also include zwitterionic and amphoteric surfactants. Suitable amphoteric and zwitterionic surfactants are, for example, derivatives of mono- or di-$C_8$–$C_{24}$ secondary and tertiary amines, such as alkyl imino acetates, carboxylates, sulfonates, sulfates, phosphates, and phosphonates, including iminodialkanoates and aminoalkanoates of the formulas $RN(CH_2)_m CO_2 M_2$ and $RNH(CH_2)_m CO_2M$, where m varies from 1 to 4, R is $C_8$–$C_{30}$ alkyl; preferably, $C_{12}$–$C_{22}$ alkyl, and M is H, alkali metal, alkaline earth metal ammonium, or alkanolammonium.

Other suitable amphoteric and zwitterionic surfactants are imidazolinium and ammonium derivates. Suitable examples of such amphoteric surfactants include sodium 3-dodecyl-aminopropionate, sodium 3-dodecylaminopropane sulfonate, N-alkyltaurines; N-higher alkyl aspartic acids, and coamidopropyl PG-dimonium chloride phosphate. For further examples of suitable amphoteric and zwitterionic surfactants, please see U.S. Pat. Nos. 2,658,072, 2,438,091, and 2,528,378, which are incorporated herein by reference Yet other suitable amphoteric and zwitterionic surfactants are betaines. Examples of suitable betaines include coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines, oleyl betaine, and cocamidopropyl betaine.

Sunscreen Compounds

A wide variety of sunscreen compounds are suitable for use with the compositions of the present invention. Depending on the nature of the composition, the sunscreen compounds may be added in the amount of up to about 40% by weight of the composition, preferably, from about 1% to about 30%. However, the preferred amount may vary depending on the nature of the composition. Thus, for the final product compositions in the form of a shampoo or conditioner, the suitable sunscreen agent may be included in the amount of up to about 40% by weight of the composition, preferably, from about 0.5% to about 5%, more preferably, from about 05 to about 1.5% by weight of the composition. Suitable sunscreen compounds include, for example, p-aminobenzoic acid, its salts and its derivatives; anthranilates; salicylates; cinnamic acid derivatives; dihydroxycinnamic acid derivatives; trihydroxycinnamic acid derivatives; hydrocarbons; dibenzalacetone and benzalacetophenone; naphtholsulfonates; dihydroxy-naphtholic acid and its salts; coumarin derivatives; diazoles; quinine salts; quinoline derivatives; hydroxy- or methoxy-substituted benzophenones; uric and vilouric acids; tannic acid and its derivatives; hydroquinone; amino benzoates, salicylates, ferrulic acid derivatives, phenylbenzimidazole sulfonic acids, benzophenone sulfonic acids, thioctic acids derivatives, oil-soluble cinnamates, and benzophenones. For other suitable sunscreen compounds, please see Segarin, et al., Cosmetics Science and Technology, Chapter VIII, pages 189 et seq., incorporated herein by reference.

Specific suitable sunscreen compounds include 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl-4->bis(hydroxypropyl)!-aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl p-dimethylaminobenzoate, 2-phenylbenzimidazole-5-sulfonic acid, 2-(p-dimethylaminophenyl)-5-sulfonicbenzoxazoic acid, para-aminobenzoic acid, benzophenone-1, benzophenone-1, benzophenone-2, benzophenone-3, benzophenone-4, benzophenone-5, benzophenone-6, benzophenone-8, benzophenone-12, methoxycinnamate, avobenzone, ethyl dihydroxypropyl para-aminobenzoate, glyceryl para-aminobenzoate, methyl anthranilate, octocrylene, octyl dimethyl para-aminobenzoate, octyl methoxycinnamate, octyl salicylate, zinc oxide, titanium dioxide, and red petrolatum.

Emollients

The compositions of the invention may also include one or additional emollient compounds such as fats, waxes, lipids, silicones, hydrocarbons, fatty alcohols and a wide variety of solvent materials. The amount of the emollient depends on the application. For the final product compositions, emollients are generally included in the amount of up to 50% by weight of the composition, preferably, from about 0.1% to about 20%, and more preferably, from about 0.5% to about 10% by weight of the composition.

Examples of suitable emollients include $C_{8-30}$ alkyl esters of $C_{8-30}$ carboxylic acids; $C_{1-6}$ diol monoesters and diesters of $C_{8-30}$ carboxylic acids; monoglycerides, diglycerides, and triglycerides of $C_{8-30}$ carboxylic acids, cholesterol esters of $C_{8-30}$ carboxylic acids, cholesterol, and hydrocarbons. Examples of these materials include diisopropyl adipate, isopropyl myristate, isopropyl palmitate, ethylhexyl palmitate, isodecyl neopentanoate, $C_{12-15}$ alcohols benzoates, diethylhexyl maleate, PPG-14 butyl ether, PPG-2 myristyl ether propionate, cetyl ricinoleate, cholesterol stearate, cholesterol isosterate, cholesterol acetate, jojoba oil, cocoa butter, shea butter, lanolin, lanolin esters, mineral oil, petrolatum, and straight and branched $C_{16}$–$C_{30}$ hydrocarbons.

Also useful are straight and branched chain fatty $C_8$–$C_{30}$ alcohols, for example, stearyl alcohol, isostearyl alcohol, ehenyl alcohol, cetyl alcohol, isocetyl alcohol, and mixtures thereof. Examples of other suitable emollients are disclosed in U.S. Pat. No. 4,919,934; which is incorporated herein by reference in its entirety.

Other suitable emollients are various alkoxylated ethers, diethers, esters, diesters, and trimesters. Examples of suitable alkoxylated ethers include PPG-10 butyl ether, PPG-11 butyl ether, PPG-12 butyl ether, PPG-13 butyl ether, PPG-14 butyl ether, PPG-15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butyleneglycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, and mixtures thereof.

Examples of alkoxylated diethers include PPG-10 1,4-butanediol diether, PPG-12 1,4-butanediol diether, PPG-14 1,4-butanediol diether, PPG-2 butanediol diether, PPG-10 1,6-hexanediol diether, PPG-12 1,6-hexanediol diether, PPG-14 hexanediol diether, PPG-20 hexanediol diether, and mixtures thereof. Preferred are those selected from the group consisting of PPG-10 1,4-butanediol diether, PPG-12 1,4-butanediol diether, PPG-10 1,6-hexandiol diether, and PPG-12 hexanediol diether, and mixtures thereof.

Suitable lipids include $C_8$–$C_{20}$ alcohol monosorbitan esters, $C_8$–$C_{20}$ alcohol sorbitan diesters, $C_8$–$C_{20}$ alcohol sorbitan triesters, $C_8$–$C_{20}$ alcohol sucrose monoesters, $C_8$–$C_{20}$ alcohol sucrose diesters, $C_8$–$C_{20}$ alcohol sucrose triesters, and $C_8$–$C_{20}$ fatty alcohol esters of $C_2$–$C_{62}$-hydroxy acids. Examples of specific suitable lipids are sorbitan diisostearate, sorbitan dioleate, sorbitan distearate, sorbitan isosotearate, sorbitan laurate, sorbitan oleate, sorbitan palmitate, sorbitan sesquioleate, sorbitan esquistearte, sorbitan stearate, sorbitan triiostearte, sorbitan trioleate, orbitan tristearate, sucrose cocoate, sucrodilaurate, sucrose distearate, sucrose laurate, sucrose myristate, sucrose oleate, sucrose palmitate, sucrose ricinoleate, sucrose stearate, sucrose tribehenate, sucrose tristearate, myristyl lactate, stearyl lactate, isostearyl lactate, cetyl lactate, palmityl lactate, cocoyl lactate, and mixtures thereof.

Other suitable emollients include mineral oil, petrolatum, cholesterol, dimethicone, dimethiconol, stearyl alcohol, cetyl alcohol, behenyl alcohol, diisopropyl adipate, isopropyl myristate, myristyl myristate, cetyl ricinoleate, sorbitan distearte, sorbitan dilaurate, sorbitan stearate, sorbitan laurate, sucrose laurate, sucrose dilaurate, sodium isostearyl lactylate, lauryl pidolate, sorbitan stearate, stearyl acohol, cetyl alcohol, behenyl alcohol, PPG-14 butyl ether, PPG-15 stearyl ether, and mixtures thereof.

Emulsifiers

The compositions of the invention may also include various emulsifiers. In the final product compositions of the invention, emulsifiers may be included in the amount of up to about 10%, preferably, in the amount of from about 0.5% to about 5% by weight of the composition. The examples of suitable emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, polyethyleneglycols, polypropyleneglyocis, and mixtures thereof.

Anti-Dandruff Compounds

The compositions of the invention may also include antidandruff agents. The examples of suitable antidandruff agents include zinc pyrithione, sulphur, and selenium sulfide.

Hair Oxidizers

The compositions of the invention may also include hair oxidizing/reducing agents. The examples of suitable hair oxidizing/reducing agents include hydrogen peroxide, perborate, thioglycolates and persulfate salts.

Thickeners

The compositions of the invention may also include various thickeners, such as cross-linked acrylates, nonionic polyacrylamides, xanthan gum, guar gum, gellan gum, and the like; polyalkyl siloxanes, polyaryl siloxanes, and aminosilicones. In the final product compositions of the invention, thickeners may be included in the amount of up to about 10%, preferably, in the amount of from about 0.2% to about 5% by weight of the composition.

The specific examples of the suitable thickening silicon compounds include polydimethylsiloxane, phenylsilicone, polydiethylsiloxane, and polymethylphenylsiloxane. Some of the suitable silicon compounds are described in European Patent Application EP 95,238 and U.S. Pat. No. 4,185,017, which are incorporated herein by reference. The compositions of the invention may also include silicone polymer materials, which provide both style retention and conditioning benefits to the hair. Such materials are described in U.S. Pat. No. 4,902,499, which is incorporated herein by reference.

Hair Conditioning Agents

The compositions of the invention may also include hydrolyzed animal protein hair conditioning agents. Croda Incorporated sells an example of a commercially available material under the tradename Crotein Q-RTM. Other examples include urea, glycerol, and propoxylated glycerols, including those described in U.S. Pat. No. 4,976,953, which is incorporated by reference herein.

Hair Setting Agents

The compositions of the invention may also include hair-setting agents to impart styling benefits upon application to hair. The hair setting polymers may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or non-ionic.

Examples of anionic monomers include unsaturated carboxylic acid monomers such as acrylic acid, methacrylic acid, maleic acid, maleic acid half ester, itaconic acid, fumaric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

Examples of cationic monomers include monomers derived from acrylic acid or methacrylic acid, and a quaternarized epihalohydrin product of a trialkylamine having 1 to 5 carbon atoms in the alkyl such as (meth)acryloxypropyltrimethylammonium chloride and (meth)acryloxypropyl-triethylammonium bromide; amine derivatives of methacrylic acid or amine derivatives of methacrylamide derived from methacrylic acid or methacrylamide and a dialkylalkanolamine having $C_1$–$C_6$ alkyl groups such as dimethylaminoethyl (meth)acrylate, diethylaminoethyl (meth)acrylate, dimethylaminopropyl (meth)acrylate, or dimethylaminopropyl (meth)acrylamide.

Examples of the amphoteric monomers include zwitterionized derivatives of the aforementioned amine derivatives of (meth)acrylic acids or the amine derivatives of (meth)acrylamide such as dimethylaminoethyl (meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth)acrylic acid or (meth)acrylamide, as discussed above, modified with propanesultone.

Examples of nonionic monomers are acrylic or methacrylic acid esters of $C_1$–$C_{24}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene; chlorostyrene; vinyl esters such as vinyl acetate; vinyl chloride; vinylidene chloride; acrylonitrile; alpha-methylstyrene; t-butylstyrene; butadiene; cyclohexadiene; ethylene; propylene; vinyl toluene; alkoxyalkyl (meth)acrylate, methoxy ethyl (meth)acrylate, butoxyethyl (meth)acrylate; allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl (meth)acrylate, n-butyl methacrylate, isobutyl methacrylate, 2-ethylhexyl methacrylate, methyl methacrylate, t-butylacrylate, t-butylmethacrylate, and mixtures thereof.

Examples of anionic hair styling polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid.

Examples of cationic hair styling polymers are copolymers of amino-functional acrylate monomers such as lower alkylamino alkyl acrylate or methacrylate monomers such as dimethyl aminoethylmethacrylate with compatible monomers such as N-vinylpyrrolidone or alkyl methacrylates such as methyl methacrylate and ethyl methacrylate and alkyl acrylates such as methyl acrylate and butyl acrylate.

Miscellaneous Components

The compositions of the invention may also include a wide range of miscellaneous ingredients. Some suitable miscellaneous ingredients commonly used in the cosmetic and personal care industry are described in The CTFA Cosmetic Ingredient Handbook, ($2^{nd}$ Ed., 1992), which is incorporated by reference herein.

Thus, the compositions of the invention may also include one or more absorbents, anti-acne agents, anti-perspirants, anticaking agents, antifoaming agents, antimicrobial agents, antioxidants, antidandruff agents, astringents, binders, buffers, biological additives, buffering agents, bulking agents, chelating agents, chemical additives, coupling agents, conditioners, colorants, cosmetic astringents, cosmetic biocides, denaturants, drug astringents, detergents, dispersants, external analgesics, film formers, foaming agents, fragrance components, humectants, keratolytics, opacifying agents, pH adjusters, preservatives, propellants, proteins, retinoids, reducing agents, sequestrants, skin bleaching agents, skin-conditioning agents (humectants, miscellaneous, and occulsive), skin soothing agents, skin healing agents, softeners, solubilizing agents, lubricants, penetrants, plastisizers, solvents and co-solvents, sunscreening additives, salts, essential oils, and vitamins.

The examples of suitable pH adjusters include sodium hydroxide, triethanoleamine, and aminomethylpropanol, and mixtures thereof. If pH adjusters are present in a final product composition, the amount may vary from about 0.01% to about 5%, preferably, from about 0.1% to about 2% by weight of the composition.

The examples of suitable film formers include glycerin/diethylene glycol myrystate copolymer, glycerin/diethylene glycol adipate copolymer, ethyl ester of PVM/MA copolymer, PVP/dimethiconylacrylate/polycarbamyl/polyglycol ester, and mixtures thereof. If the film formers are present in the final product compositions, the amount may vary from about 0.1% to about 15.0% by weight of the composition, preferably, from about 0.1% to about 2.5% by weight of the composition.

The examples of suitable vitamins include tocopherol, tocopherol acetate, retinoic acid, retinol, and retinoids.

The examples of suitable anti-acne medicaments include resorcinol, sulfur, salicylic acid, erythromycin, zinc, and benzoyl peroxide.

The examples of suitable skin bleaching or lightening agents include hydroquinone, and kojic acid. The examples of suitable aesthetic components such as fragrances, pigments, colorings, and the like, include panthenol and derivatives (e.g., ethyl panthenol), aloe vera, pantothenic acid and its derivatives, clove oil, menthol, camphor, eucalyptus oil, eugenol, menthyl lactate, witch hazel distillate, allantoin, bisabolol, and dipotassium glycyrrhizinate.

The ingredients described in U.S. Pat. Nos. 5,693,316, 5,597,555, 5,455,025, and 5,302,377, which are thus incorporated herein by reference, may also be used in the compositions of the invention to the extent such use is commensurate with overall description of the compositions provided herein.

The invention is further illustrated in reference to the following non-limiting examples that follow.

EXAMPLE 1

Preparation of PPG-3 Benzyl Ether 2297.75 g (21.24 moles) of benzyl alcohol was placed in a dry, stirred pressure vessel fitted with a nitrogen inlet. A catalytic amount (6 g) of KOH was added as a 40% aqueous solution. The vessel was purged with nitrogen and heated to 110° C. Vacuum was applied for 1 hour to remove the water vapors from the headspace of the vessel, and the mixture was further heated to 130° C. After 3702.25 g (63.74 moles) of propylene oxide were added, the reaction mixture was stirred for additional 3 hours to complete the reaction. The progress of the reaction was monitored by the uptake of the reagent and the measurement of the pressure in the vessel. The reaction mixture was cooled to 110° C., and a vacuum was applied for approximately 1 hour. To neutralize KOH in the reaction mixture, 29 g of 25% sulfuric acid was added. The mixture was stirred for 10 minutes, and the pH was adjusted to 5.7. Upon cooling, PPG-3 Benzyl Ether, a thin light yellow liquid, was isolated as the major product.

EXAMPLE 2

Preparation of PPG-3 Benzyl Myristate

A four-necked flask, fitted with a mechanical stirrer, a thermometer and a nitrogen inlet was charged with 342.44 g (1.19 moles) of PPG-3 benzyl ether, a 221 g (1.13 moles) of myristic acid and 0.45 g of SnO. The mixture was heated to 220° C. The progress of the reaction was monitored by measuring the acid value of the reaction mixture over time. Once the acid value was stable, the mixture was cooled to 25° C. 0.9 g of 30% aqueous solution of $H_2O_2$ and 70 g of water were added, and the mixture was heated again to 75° C. The water was evaporated under vacuum, producing PPG-3 Benzyl Myristate as the major product.

EXAMPLE 3

Preparation of di-(PPG-4) Bisphenol A Ether

To a clean, dry stirred tank pressure vessel with nitrogen inlet is charged 1233.86 g (5.40 moles) of bisphenol A and 1445 mLs of Toluene. The vessel is purged with nitrogen and a catalytic amount (4.86 g) of $BF_3$/Etherate Solution is charged. The temperature is raised to 110° C. and 2511.29 g (43.24 moles) of Propylene Oxide is added at a constant rate to keep the pressure inside the vessel below 50 psig. After all Propylene Oxide is added, the reaction mixture is allowed to react for an additional 3 hours after which the temperature is raised to 150° C. and the toluene is distilled off under nitrogen sparge. After the distillation of Toluene, the temperature is cooled to 110° C. and vacuum is applied for 1 hour.

EXAMPLE 4

Preparation of di-(PPG-4) Bisphenol A Monolaurate

To a four neck round bottom flask fitted with nitrogen inlet, mechanical stirrer, temperature probe and condenser is charged 700 g (1.01 moles) of the Propoxylate from example 3 and 202.32 g (1.01 moles) of Lauric Acid. A catalytic amount of Methanesulfonic Acid (0.90 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 5

Preparation of di-(PPG-4) Bisphenol A Distearate

To a four neck round bottom flask fitted with nitrogen inlet, mechanical stirrer, temperature probe and condenser is charged 700 g (1.01 moles) of the Propoxylate from example 3 and 550.80 g (1.95 moles) of Stearic Acid. A catalytic amount of Methanesulfonic Acid (1.25 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 6

Preparation of di-(PEG-3, PPG-4) Bisphenol A Ether

To a clean, dry stirred tank pressure vessel with nitrogen inlet is charged 2000 g (2.89 moles) of the Propoxylate from example 1 and a catalytic amount (9.33 g) of 45% KOH. The vessel is purged with nitrogen and heated to 110° C. Vacuum is applied for 1 hour to remove trace amounts of water and the temperature is raised to 150° C. Ethylene Oxide in the amount of 762.83 g (17.34 moles) is added at a constant rate to keep the pressure below 50 psig. After all Ethylene Oxide is added, the reaction mixture is allowed to react for an additional hour after which the temperature is lowered to 110° C. and vacuum is applied for one hour. The reaction mixture is cooled to 65° C. and the catalyst is neutralized with an equivalent molar amount of 25% Sulfuric Acid.

EXAMPLE 7

Preparation of di-(PEG-3, PPG-4) Bisphenol A Monomyristate

To a four neck round bottom flask fitted with nitrogen inlet, mechanical stirrer, temperature probe and condenser is charged 1000 g (1.05 moles) of the Alkoxylate from example 6 and 239.79 g (1.05 moles) of Myristic Acid. A catalytic amount of Methanesulfonic Acid (1.24 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 8

Preparation of di-(PEG-3, PPG-4) Bisphenol A Dioleate

To a four neck round bottom flask fitted with nitrogen inlet, mechanical stirrer, temperature probe and condenser is charged 1000 g (1.05 moles) of the Alkoxylate from example 6 and 575.59 g (2.05 moles) of Oleic Acid. A catalytic amount of Methanesulfonic Acid (1.58 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 9

Preparation of di-(PEG-2 PPG-2) Bisphenol A Ether

To a clean, dry stirred tank pressure vessel with nitrogen inlet is charged 1342.52 g (5.88 moles) of bisphenol A and 1445 mLs of Toluene. The vessel is purged with nitrogen and a catalytic amount (5.00 g) of $BF_3$/Etherate Solution is charged. The temperature is raised to 110° C. and a mixture of 1366.22 g (23.52 moles) of Propylene Oxide and 1036.19 g (23.52 moles) of Ethylene Oxide is added at a constant rate to keep the pressure inside the vessel below 50 psig. After all Propylene Oxide/Ethylene Oxide is added, the reaction mixture is allowed to react for an additional 3 hours after which the temperature is raised to 150° C. and the toluene is distilled off under nitrogen sparge. After the distillation of Toluene, the temperature is cooled to 110° C. and vacuum is applied for 1 hour.

EXAMPLE 10

Preparation of di-(PEG-2 PPG-2) Bisphenol A Monopalmitate

To a four neck round bottom flask fitted with nitrogen inlet, mechanical stirrer, temperature probe and condenser is charged 1140.69 g (1.79 moles) of the Alkoxylate from example 9 and 459.31 g (1.79 moles) of Palmitic Acid. A catalytic amount of Methanesulfonic Acid (1.6 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 11

Preparation of di-(PEG-2 PPG-2) Bisphenol A Dibehenate

To a four neck round bottom flask fitted with nitrogen inlet, mechanical stirrer, temperature probe and condenser is charged 783.20 g (1.23 moles) of the Alkoxylate from example 9 and 816.80 g (2.40 moles) of Behenic Acid. A catalytic amount of Methanesulfonic Acid (1.6 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 12

Preparation PPG-4 2-Naphthol Ether

To a clean, dry stirred tank pressure vessel with nitrogen inlet is charged 1434.05 g (9.95 moles) of 2-Naphthol and 1445 mLs of Toluene. The vessel is purged with nitrogen and a catalytic amount (4.97 g) of $BF_3$/Etherate Solution is charged. The temperature is raised to 110° C. and 2310.86 g (39.79 moles) of Propylene Oxide is added at a constant rate to keep the pressure inside the vessel below 50 psig. After all Propylene Oxide is added, the reaction mixture is allowed to react for an additional 3 hours after which the temperature is raised to 150° C. and the toluene is distilled off under nitrogen sparge. After the distillation of Toluene, the temperature is cooled to 110° C. and vacuum is applied for 1 hour.

EXAMPLE 13

Preparation of PPG-4 2-Naphthyl Myristate

To a four neck round bottom flask fitted with nitrogen inlet, mechanical stirrer, temperature probe and condenser is charged 500 g (1.33 moles) of the Propoxylate from example 12 and 289.15 g (1.27 moles) of Myristic Acid. A catalytic amount of Methanesulfonic Acid (0.80 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 14

Preparation of PPG-4 2-Naphthyl Caprate

To a four neck round bottom flask fitted with nitrogen inlet, mechanical stirrer, temperature probe and condenser is charged 500 g (1.33 moles) of the Propoxylate from example 12 and 218.80 g (1.27 moles) of Capric Acid. A catalytic amount of Methanesulfonic Acid (0.70 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 15

Preparation of PEG-5 PPG-4 2-Naphthol Ether

To a clean, dry stirred tank pressure vessel with nitrogen inlet is charged 2000 g (5.31 moles) of the Propoxylate from example 10 and a catalytic amount (10.67 g) of 45% KOH. The vessel is purged with nitrogen and heated to 110° C. Vacuum is applied for 1 hour to remove trace amounts of water and the temperature is raised to 150° C. Ethylene Oxide in the amount of 1169.53 g (26.55 moles) is added at a constant rate to keep the pressure below 50 psig. After all Ethylene Oxide is added, the reaction mixture is allowed to react for an additional hour after which the temperature is lowered to 110° C. and vacuum is applied for one hour. The reaction mixture is cooled to 65° C. and the catalyst is neutralized with an equivalent molar amount of 25% Sulfuric Acid.

EXAMPLE 16

Preparation of PEG-5 PPG-4 2-Naphthyl Oleate

To a four neck round bottom flask fitted with nitrogen inlet, mechanical stirrer, temperature probe and condenser is charged 1102.84 g (1.85 moles) of the Alkoxylate from example 15 and 497.16 g (1.76 moles) of Oleic Acid. A catalytic amount of Methanesulfonic Acid (1.6 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 17

Preparation of PEG-5 PPG-4 2-Naphthyl Stearate

To a four neck round bottom flask fitted with nitrogen inlet, mechanical stirrer, temperature probe and condenser is charged 1100.40 g (1.84 moles) of the Alkoxylate from example 15 and 499.60 g (1.76 moles) of Stearic Acid. A catalytic amount of Methanesulfonic Acid (1.6 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 18

Preparation of PEG-3 PPG-5 2-Naphthol Ether

To a clean, dry stirred tank pressure vessel with nitrogen inlet is charged 952.71 g (6.61 moles) of 2-Naphthol and 1445 mLs of Toluene. The vessel is purged with nitrogen and a catalytic amount (4.96 g) of BF$_3$/Etherate Solution is charged. The temperature is raised to 110° C. and a mixture of 1919.03 g (33.04 moles) of Propylene Oxide and 873.28 g (19.82 moles) of Ethylene Oxide is added at a constant rate to keep the pressure inside the vessel below 50 psig. After all Propylene Oxide/Ethylene Oxide is added, the reaction mixture is allowed to react for an additional 3 hours after which the temperature is raised to 150° C. and the toluene is distilled off under nitrogen sparge. After the distillation of Toluene, the temperature is cooled to 110° C. and vacuum is applied for 1 hour.

EXAMPLE 19

Preparation of PEG-3 PPG-5 2-Naphthyl Laurate

To a four neck round bottom flask fitted with nitrogen inlet, mechanical stirrer, temperature probe and condenser is charged 1197.03 g (2.11 moles) of the Alkoxylate from example 18 and 402.97 g (2.01 moles) of Lauric Acid. A catalytic amount of Methanesulfonic Acid (1.6 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 20

Preparation of PEG-3 PPG-5 2-Naphthyl Behenate

To a four neck round bottom flask fitted with nitrogen inlet, mechanical stirrer, temperature probe and condenser is charged 1017.59 g (1.80 moles) of the Alkoxylate from example 18 and 582.41 g (1.71 moles) of Lauric Acid. A catalytic amount of Methanesulfonic Acid (1.6 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 21

Preparation of PPG-6 2-Phenoxyethanol Ether

To a clean, dry stirred tank pressure vessel with nitrogen inlet is charged 1419.53 g (10.27 moles) of 2-Phenoxyethanol and a catalytic amount (16.67 g) of 45% KOH. The vessel is purged with nitrogen and heated to 110° C. Vacuum is applied for 1 hour to remove trace amounts of water and the temperature is raised to 150° C. Propylene Oxide in the amount of 3580.47 g (61.65 moles) is added at a constant rate to keep the pressure below 50 psig. After all Propylene Oxide is added, the reaction mixture is allowed to react for an additional hour after which the temperature is lowered to 110° C. and vacuum is applied for one hour. The reaction mixture is cooled to 65° C. and the catalyst is neutralized with an equivalent molar amount of 25% Sulfuric Acid.

EXAMPLE 22

Preparation of PPG-6 2-Phenoxyethyl Caprate

To a four neck round bottom flask fitted with nitrogen inlet, mechanical stirrer, temperature probe and condenser is charged 500 g (1.03 moles) of the Propoxylate from example 21 and 168.84 g (0.98 moles) of Capric Acid. A catalytic amount of Methanesulfonic Acid (0.67 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 23

Preparation of PPG-6 2-Phenoxyethyl Palmitate

To a four neck round bottom flask fitted with nitrogen inlet, mechanical stirrer, temperature probe and condenser is charged 500 g (1.03 moles) of the Propoxylate from example 21 and 251.29 g (0.98 moles) of Palmitic Acid. A catalytic amount of Methanesulfonic Acid (0.75 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 24

Preparation of PEG-4 PPG-6 2-Phenoxyethanol Ether

To a clean, dry stirred tank pressure vessel with nitrogen inlet is charged 2000 g (4.11 moles) of the Propoxylate from example 21 and a catalytic amount (9.33 g) of 45% KOH. The vessel is purged with nitrogen and heated to 110° C. Vacuum is applied for 1 hour to remove trace amounts of water and the temperature is raised to 150° C. Ethylene Oxide in the amount of 724.18 g (16.44 moles) is added at a constant rate to keep the pressure below 50 psig. After all Ethylene Oxide is added, the reaction mixture is allowed to react for an additional hour after which the temperature is lowered to 110° C. and vacuum is applied for one hour. The reaction mixture is cooled to 65° C. and the catalyst is neutralized with an equivalent molar amount of 25% Sulfuric Acid.

EXAMPLE 25

Preparation of PEG-4 PPG-6 2-Phenoxyethyl Laurate

To a four neck round bottom flask fitted with nitrogen inlet, mechanical stirrer, temperature probe and condenser is charged 1242.41 g (1.87 moles) of the Alkoxylate from example 24 and 357.59 g (1.79 moles) of Lauric Acid. A catalytic amount of Methanesulfonic Acid (1.6 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 26

Preparation of PEG-4 PPG-6 2-Phenoxyethyl Myristate

To a four neck round bottom flask fitted with nitrogen inlet, mechanical stirrer, temperature probe and condenser is charged 1204.70 g (1.82 moles) of the Alkoxylate from example 24 and 395.30 g (1.73 moles) of Myristic Acid. A catalytic amount of Methanesulfonic Acid (1.6 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 27

Preparation of PEG-3 PPG-3 2-Phenoxyethanol Ether

To a clean, dry stirred tank pressure vessel with nitrogen inlet is charged 1553.93 g (11.25 moles) of 2-Phenoxyethanol and a catalytic amount (16.67 g) of 45% KOH. The vessel is purged with nitrogen and heated to 110° C. Vacuum is applied for 1 hour to remove trace amounts of water and the temperature is raised to 150° C. A mixture of 1919.03 g (33.04 moles) of Propylene Oxide and 873.28 g (19.82 moles) of Ethylene Oxide is added at a constant rate to keep the pressure below 50 psig. After all Propylene Oxide/Ethylene Oxide is added, the reaction mixture is allowed to react for an additional hour after which the temperature is lowered to 110° C. and vacuum is applied for one hour. The reaction mixture is cooled to 65° C. and the catalyst is neutralized with an equivalent molar amount of 25% Sulfuric Acid.

EXAMPLE 28

Preparation of PEG-3 PPG-3 2-Phenoxyethyl Behenate

To a four neck round bottom flask fitted with nitrogen inlet, mechanical stirrer, temperature probe and condenser is charged 925.05 g (2.08 moles) of the Alkoxylate from example 27 and 674.95 g (1.98 moles) of Behenic Acid. A catalytic amount of Methanesulfonic Acid (1.6 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 29

Preparation of PEG-3 PPG-3 2-Phenoxyethyl Stearate

To a four neck round bottom flask fitted with nitrogen inlet, mechanical stirrer, temperature probe and condenser is charged 994.13 g (2.24 moles) of the Alkoxylate from example 27 and 605.87 g (2.13 moles) of Stearic Acid. A catalytic amount of Methanesulfonic Acid (1.6 g) is charged and the reaction mixture is heated to 220° C. under nitrogen sparge. The reaction is monitored by measuring the acid value to an AV of preferably less than 5. Once the AV is reached, the temperature is cooled to 85° C. and the catalyst is neutralized with an equivalent molar amount of 45% KOH and washed once with water. The reaction is dried under vacuum yielding the desired product.

EXAMPLE 30

Solubility Tests for Benzophenone-3

The solubility of benzophenone-3 in the compounds of the invention was compared with its solubility in a mixture of $C_{12}$–$C_{15}$ benzyl esters described in U.S. Pat. No. 4,275,222, which is incorporated herein by reference. The compositions of the test solutions were as follows:

| Test solution | Benzophenone-3 (g) | Mixture of $C_{12}$–$C_{15}$ benzoic acid esters (g) | PPG-3 benzyl myristate (g) |
|---|---|---|---|
| A | 3 | 17 | — |
| B | 3 | — | 17 |
| C | 4 | 16 | — |
| D | 4 | — | 16 |

A. Preparation Procedure for Test Solutions

To prepare the test solutions, appropriate amounts of Benzophenone-3 was weighed and transferred to a 50-ml beaker equipped with a small stirring bar. The correct amount of the desired ester was added to the beaker and the contents of the beaker were heated on a pre-warmed 70–75° C. hot plate. Once the entire solid has dissolved, the solution was heated for additional 10 minutes. Care was taken to make sure that no solid remained on the sides of the beaker. After 10 minutes, the beaker was removed from the hot plate and placed on a cool stir plate to allow the solution to cool with stirring to approximately 35° C. The solution was transferred to a 2-ounce jar. The contents of the jar remained undisturbed for 24 hours in a 25° C. water bath. After 24 hours, the jars were visually inspected for evidence and degree of crystallization.

B. Test Results

There was no crystal formation for test solutions A and B. Crystal formation was observed for test solutions C and D. The amount of crystals formed in test solution C was approximately three times greater than in test solution D.

EXAMPLE 31

Sunscreen Lotion 1

A sunscreen lotion may include the following ingredients, including PPG-3 Benzyl Myristate:

| Phase A | |
|---|---|
| Ingredient(s) | % W/W |
| Crodafos CES (Cetearyl Alcohol (and) Dicetyl Phosphate (and) Ceteth-10 Phosphate) | 8.0 |
| PPG-3 Benzyl Myristate | 25.0 |
| Benzophenone 3 | 5.0 |
| Octyl Methoxycinnamate | 7.5 |

| Phase B | |
|---|---|
| Ingredient | W/W % |
| Water | 53.25 |
| Potassium Hydroxide | 0.25 |

| Phase C | |
|---|---|
| Ingredient | W/W % |
| Germaben II (preservative) | 1.0 |

The ingredients of Phase A are combined and heated to 75° C. In a separate vessel, the ingredients of Phase B are also combined and heated to 75° C. Phase A is added to Phase B with stirring, and the stirring is continued while the combined phases are cooled to 40° C. Phase C is added, the cooling is continued to 25° C., providing the desired lotion.

EXAMPLE 32

Sunscreen Spray Lotion

A sunscreen spray lotion may include the following ingredients, including PPG-3 Benzyl Myristate:

| Phase A | |
|---|---|
| Ingredient | % W/W |
| Crodafos CS20 Acid (Dicetyl Phosphate, Ceteth-20 Phosphate and Cetearyl Alcohol) | 5.0 |
| PPG-3 Benzyl Myristate | 10.0 |
| Benzophenone 3 | 6.0 |
| Octyl Methoxycinnamate | 7.5 |
| Menthyl Anthranilate | 5.0 |
| Cromollient SCE (Di-PPG-2 Myreth-10 Adipate) | 3.0 |

| Phase B | |
|---|---|
| Ingredient | W/W % |
| Water | 62.4 |
| Sodium Hydroxide | 0.1 |

| Phase C | |
|---|---|
| Ingredient | W/W % |
| Germaben II (preservative) | 1.0 |

The ingredients of Phase A are combined and heated to 75° C. In a separate vessel, the ingredients of Phase B are also combined and heated to 75° C. Phase A is added to Phase B with stirring, and the stirring is continued while the combined phases are cooled to 40° C. Phase C is added, the cooling is continued to 25° C., providing the desired lotion.

EXAMPLE 33

Sunscreen Lotion 2

| Ingredient(s) | % W/W |
|---|---|
| Phase A | |
| PPG-8 Bisphenol A Distearate | 2.0 |
| Crodafos CS20 Acid (Cetearyl Alcohol (and) Ceteth-20 Phosphate (and) Dicetyl Phosphate) | 4.0 |
| Cetearyl Alcohol | 4.0 |
| PPG-3 Benzyl Myristate | 15.0 |
| Benzophenone 3 | 5.0 |
| Octyl Methoxycinnamate | 7.5 |
| Phase B | |
| Water | 61.50 |
| Phase C | |
| Germaben II (preservative) | 1.0 |

Procedure: Combine Phase A and heat to 75 C°. In a separate vessel, combine Phase B and heat to 75° C. Add Phase A to Phase B while stirring and continue stirring while allowing cooling to 40C. Add Phase C and continue cooling to 25° C.

EXAMPLE 34

Cationic Sunscreen Lotion

| Ingredient(s) | % W/W |
| --- | --- |
| Phase A | |
| Behentrimonium Methosulfate | 2.0 |
| PPG-8 Bisphenol A Monolaurate | 3.0 |
| Cetearyl Alcohol | 4.0 |
| Crodamol OS (Octyl Stearate) | 15.0 |
| Benzophenone 3 | 5.0 |
| Octyl Methoxycinnamate | 7.5 |
| Phase B | |
| Water | 62.5 |
| Phase C | |
| Germaben II (preservative) | 1.0 |

Procedure: Combine Phase A and heat to 75C. In a separate vessel, combine Phase B and heat to 75C. Add Phase A to Phase B while stirring and continue stirring while allowing to cool to 40C. Add Phase C and continue cooling to 25C.

EXAMPLE 35

Moisturizing Lotion

| Ingredient | % W/W | % W/W | % W/W |
| --- | --- | --- | --- |
| Phase A | | | |
| Cetearyl Alcohol | 4.0 | 4.0 | 4.0 |
| Crodamol OS (Octyl Stearate) | 5.0 | 5.0 | 5.0 |
| PEG-3, PPG-3 Phenoxyethyl Behenate | 5.0 | 0.0 | 0.0 |
| PPG-3 Benzyl Myristate | 0.0 | 5.0 | 0.0 |
| PEG-5, PPG-4 2-Naphthyl Oleate | 0.0 | 0.0 | 5.0 |
| Petrolatum | 3.5 | 3.5 | 3.5 |
| Dimethicone | 3.0 | 3.0 | 3.0 |
| Crodamol SS (Cetyl Esters) | 5.0 | 5.0 | 5.0 |
| Phase B | | | |
| Water | 73.28 | 73.28 | 73.28 |
| Carbopol 941 (Carbomer) (thickener) | 0.15 | 0.15 | 0.15 |
| NaOH (neutralizing agent) | 0.07 | 0.07 | 0.07 |
| Phase C | | | |
| Germaben II (preservative) | 1.0 | 1.0 | 1.0 |

Procedure: Dust the Carbopol 941 from Phase B into the water with mixing. Heat to 75–80° C. and add NaOH. Combine ingredients from Phase A and heat with mixing to 75–80° C. Add Phase B to Phase A while mixing and allow to cool to 40° C. Add Phase C with mixing and allow cooling to desired fill temperature.

EXAMPLE 36

Hair Conditioner

| Ingredient(s) | % W/W |
| --- | --- |
| Phase A | |
| Incroquat Behenyl TMS-50 (Behentrimonium Methosulfate (and) Cetearyl Alcohol) | 2.5 |
| Crodacol S-70 (Stearyl Alcohol) | 2.5 |
| PEG-5, PPG-4 2-Naphthyl Stearate | 2.0 |
| PPG-6 2-Phenoxyethyl Caprate | 1.5 |
| Phase B | |
| Water | 90.5 |
| Phase C | |
| Germaben II (preservative) | 1.0 |

Procedure: Combine Phase A and heat to 75C. In a separate vessel, combine Phase B and heat to 75C. Add Phase A to Phase B while stirring and continue stirring while allowing to cool to 40C. Add Phase C and continue cooling to 25C.

EXAMPLE 37

Conditioning Shampoo

| Ingredient(s) | % W/W |
| --- | --- |
| Phase A | |
| PEG-4, PPG-6 2-Phenoxyethyl Myristate | 4.0 |
| Ammonium Lauryl Sulfate | 25.0 |
| Ammonium Laureth Sulfate | 12.0 |
| Crosultaine C-50 (Cocamidopropyl Hydroxysultaine) | 3.0 |
| Lauramide DEA | 1.0 |
| Germaben II (Preservative) | 1.0 |
| Water | 52.0 |
| Phase B | |
| Incroquat HO-80PG (PEG-3 Dioleoylamidoethylmonium Methosulfate) | 2.0 |

Procedure: Combine Phase A and heat to 60C. Add Phase B and continue stirring while allowing to cool to 25C.

EXAMPLE 38

Conditioning Shampoo with UV Protection

| Ingredient(s) | % W/W |
| --- | --- |
| Phase A | |
| PEG-6, PPG-8 Bisphenol A Monomyristae | 4.0 |

-continued

| Ingredient(s) | % W/W |
|---|---|
| Ammonium Lauryl Sulfate | 25.0 |
| Ammonium Laureth Sulfate | 12.0 |
| Crosultaine C-50 (Cocamidopropyl Hydroxysultaine) | 3.0 |
| Lauramide DEA | 1.0 |
| Germaben II (Preservative) | 1.0 |
| Water | 50.0 |
| Phase B | |
| Polyquaternium 59 (and) Butylene Glycol | 3.0 |
| Benzophenone 3 | 1.0 |

Procedure: Combine Phase A and heat to 60C. Add Phase B and continue stirring while allowing to cool to 25C.

EXAMPLE 39

Shampoo for Improved Hair Shine and UV Protection

| Ingredient(s) | % W/W |
|---|---|
| Phase A | |
| PEG-5, PPG-4 Naphthyl Oleate | 1.0 |
| Ammonium Lauryl Sulfate | 25.0 |
| Ammonium Laureth Sulfate | 12.0 |
| Crosultaine C-50 (Cocamidopropyl Hydroxysultaine) | 3.0 |
| Lauramide DEA | 1.0 |
| Germaben II (Preservative) | 1.0 |
| Water | 53.0 |
| Phase B | |
| Polyquaternium 59 (and) Butylene Glycol | 3.0 |
| Benzophenone 3 | 1.0 |

Procedure: Combine Phase A and heat to 60C. Add Phase B and continue stirring while allowing cooling to 25C.

EXAMPLE 40

Antiperspirant Stick

| Ingredient(s) | % W/W |
|---|---|
| Procetyl AWS (PPG-5-Ceteth-20) | 49.0 |
| Crodacol C-95 (Cetyl Alcohol) | 16.0 |
| PPG-3 Benzyl Myristate | 5.0 |
| Dimethicone Cyclomethicone | 5.0 |
| Part B | |
| Aluminum Chlorhydrate | 25.0 |

Procedure: Combine Part A ingredients and heat to 60–65° C. Cool to 50–55° C. and while mixing, Part B while being careful to avoid aeration. Cool to desired fill temperature.

EXAMPLE 41

Clear Deodorant Stick

| Ingredient(s) | % W/W |
|---|---|
| Part A | |
| Sodium Stearate C-1 | 7.7 |
| Incromide CA (Cocamide DEA) | 7.0 |
| PEG-6, PPG-6 Bisphenol A Monomyristate | 2.5 |
| Propylene Glycol | 57.0 |
| Triclosan | 0.3 |
| Probutyl DB-10 (PPG-10 Butane Diol) | 7.5 |
| Part B | |
| Deionized Water | 18.0 |

Procedure: Combine all Part A ingredients ad increase temperature to 70–80° C. using high agitation. Continue stirring for 5–10 minutes once temperature is reached then slowly start adding Part B over a 5–10 minute period. Pour into molds.

EXAMPLE 42

Microemulsion Gel

| Ingredient(s) | % W/W |
|---|---|
| Part A | |
| DEA Oleth-3 Phosphate | 7.0 |
| Volpo 5 (Oleth-5) | 4.0 |
| Volpo 3 (Oleth-3) | 7.0 |
| PPG-3 Benzyl Myristate | 10.0 |
| Squalane | 10.0 |
| Part B | |
| Deionized Water | 50.0 |
| Propylene Glycol | 10.00 |
| Glycerin | 1.00 |
| Part C | |
| Glydant (preservative) | 1.00 |

Procedure: Combine all Part A ingredients with mixing and increase temperature to 90–95° C. Combine ingredients of Part B with mixing and heat to 90–95° C. Add Part A to Part B and mix at 95° C. Cool to about 70° C. and add Part C. The gel should set at this point.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A composition comprising:

at least one ester of alkoxylated aromatic alcohol and fatty carboxylic acid, having the structure

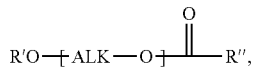

wherein R' is an organic moiety including at least one aromatic nucleus $R_N$ that may be substituted or unsubstituted, said aromatic nucleus $R_N$ having from 6 to 20 carbon atoms exclusive of substitution and wherein R' has the structure $R_N\text{—}(CH_p)_n\text{—}$, where $\text{—}(CH_p)_n\text{—}$ is an alkyl group, which may be straight-chain or branched, saturated or unsaturated, in which p is 0, 1, or 2, and n varies from 1 to 6 ;

R" is a fatty alkyl group, straight chain or branched, saturated or unsaturated, substituted or unsubstituted, having from 1 to 39 carbon atoms; and ALK—O is an alkoxy spacer having in number of units of the structure $\text{—}(R'''O)_m\text{—}$, which may be same or different, where m ranges from 1 to 300 and each R''' is an alkyl group, straight-chain or branched, saturated or unsaturated, substituted or unsubstituted, having from 1 to 6 carbon atoms, a) said ester being present in the amount of from about 0.1% to about 99% by weight of the composition, and b) at least one functional ingredient present in the amount of from about 0.1% to 60% by weight of the composition;

wherein said composition is a personal care or cosmetic product.

2. The composition of claim 1, wherein said functional ingredient is an active ingredient selected from the group consisting of sunscreen active ingredients, surfactants, moisturizers, conditioners, antiseptic agents, anti-oxidants, reducing agents, antiperspirants, and fragrances.

3. The composition of claim 2, wherein said active ingredient is the sunscreen compound selected from the group consisting of octyl methoxycinnamate, phenylbenzimidazole sulfonic acid, menthyl anthranilate, cinnamidopropyl trimonium chloride, para-aminobenzoic acid, benzophenone-1, benzophenone-2 benzophenone-3, benzophenone-4, benzophenone-5, benzophenone-6, benzophenone-8, benzophenone-12, methoxycinnamate, avobenzone, ethyl dihydroxypropyl para-aminobenzoate, glyceryl para-aminobenzoate, methyl anthranilate, octocrylene, octyl dimethyl para-aminobenzoate, octyl salicylate, zinc oxide, titanium dioxide, and red petrolatum.

4. The composition of claim 3, wherein said personal care or cosmetic product is a topical sunscreen product formulation selected from the group consisting of a suntan lotion, a sunscreen lotion, a sunscreen spray lotion, UV-protecting shampoo, and UV-protecting hair conditioner.

5. The composition of claim 1, further comprising at least one cyclomethicone compound present in the amount of from about 1% to about 40% by weight of the composition.

6. The composition of claim 5, wherein said active ingredient is an antiperspirant.

7. The composition of claim 6, wherein said personal care or cosmetic product is a topical antiperspirant product formulation selected from the group consisting of antiperspirant stick, clear deodorant stick, antiperspirant gel and antiperspirant spray.

8. The composition of claim 1, wherein said personal care or cosmetic product is selected from the group consisting of shampoos, hair conditioners, sunscreen product formulations, antiperspirants, baby shampoos, baby bath products, hand dishwashing liquids, body washes, facial washes, and baby wipes.

9. The composition of claim 1, wherein said personal care product is in the form selected from the group consisting of microemulsion gel, emulsion, liquid, solid, cream, aerosol spray and non-aerosol spray.

10. The composition of claim 2, further comprising one or more additional ingredients selected from the group consisting of emollients, emulsifiers, humectants, softeners, lubricants, penetrants, plastisizers, solvents and co-solvents, dispersants, thickening agents, preservatives, buffers, chelating agents, foaming agents, coupling agents, proteins, salts, and oils.

11. The composition of claim 1, wherein said R" ranges from 1 to 21 carbon atoms.

12. The composition of claim 11, wherein said R" ranges from 5 to 22 carbon atoms.

13. The composition of claim 12, wherein said R" ranges from 5 to 17 carbon atoms.

14. The composition of claim 1, wherein said at least one ester of alkoxylated aromatic alcohol and fatty carboxylic acid is produced by reacting the fatty carboxylic acid or a derivative thereof with the alkoxylated aromatic alcohol.

15. The composition of claim 14, wherein said alkoxylated aromatic alcohol has two hydroxy groups capable of reacting with said fatty carboxylic acid or said derivative thereof.

16. The composition of claim 15, wherein said fatty carboxylic acid is reacted with a stoichiometric excess of said alkoxylated aromatic alcohol.

17. The composition of claim 15, wherein said alkoxylated aromatic alcohol is reacted with a stoichiometric excess of said fatty carboxylic acid.

18. The composition of claim 14, wherein said alkoxylated aromatic alcohol has one hydroxy group capable of reacting with said fatty carboxylic acid or said derivative thereof.

19. The composition of claim 14, wherein said fatty carboxylic acid is selected, from the group consisting of myristic acid, propionic acid, behenic acid, erucic acid, montan acid, phenyl acetic acid, oleic acid, stearic acid, palmitic acid, coconut-oil-derived acid mixture, palm oil-derived acid mixture, and mixtures thereof.

20. The composition of claim 14, wherein said derivative of fatty carboxylic acid is selected from the group consisting of carboxylic acid anhydrides, natural oils, triglycerides, and mixtures thereof.

21. The composition of claim 14, wherein said alkoxylated aromatic alcohol is selected from the group consisting of alkoxylated benzyl alcohol, alkoxylated phenoxyethanol, alkoxylated cynnamyl alcohol, alkoxylated phenoxy-n-propanol, alkoxylated phenoxy-i-propanol, and mixtures thereof.

22. The composition of claim 14, wherein said alkoxylated aromatic alcohol is selected from the group consisting of alkoxylated bisphenol A, alkoxylated bisphenol AF, alkoxylated bisphenol AP, alkoxylated tetramethyl bisphenol A, alkoxylated bisphenol F, alkoxylated bisphenol E, alkoxylated bisphenol C, alkoxylated bisphenol M, alkoxylated bisphenol P, alkoxylated bisphenol S, alkoxylated bisphenol Z and mixtures thereof.

23. A composition comprising:

at least one ester of alkoxylated aromatic alcohol and fatty carboxylic acid selected from the group consisting of compounds of the formula (I), or (II), and mixtures thereof:

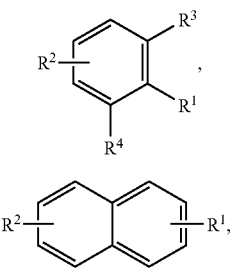

wherein $R^1$ is a group of the structure,

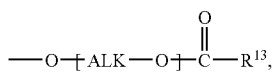

$R^2$, $R^3$, and $R^4$, which may be same or different, are each independently selected from the group consisting of hydrogen, lower alkyl, lower halogenated alkyl, hydroxy, lower alkylhydroxy, halo, lower alkoxy, a group of the structure

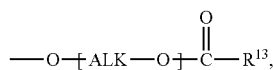

a group of the structure

a group of the structure

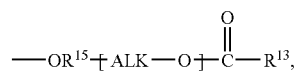

a group of the structure —O—[ALK—O]—H,
a group of the structure —R$^{14}$O—[ALK—O]—H,
a group of the structure —OR$^{15}$—[ALK—O]—H,
a group of the structure

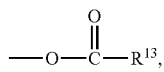

a group of the structure

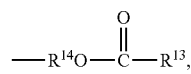

and
a group of the structure

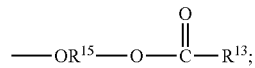

$R^{13}$, which may be same or different in each of the groups $R^1$, $R^2$, $R^3$, $R^4$, $R^5$, and $R^6$, is an alkyl group, straight chain or branched, saturated or unsaturated, substituted or unsubstituted, having 1 to 39 carbon atoms;

$R^{14}$, which may be same or different in each of the groups $R^1$, $R^2$, $R^3$, and $R^4$, is an alkyl group, straight chain or branched, saturated or unsaturated, substituted or unsubstituted, containing 1 to 6 carbon atoms;

$R^{15}$, which may be same or different in each of the groups $R^1$, $R^2$, $R^3$, and $R^4$, is an alkyl group, straight chain or branched, saturated or unsaturated, substituted or unsubstituted, containing 1 to 8 carbon atoms;

—[ALK—O]— is an alkoxy spacer that includes x units of the structure —[CH$_2$CH$_O$]— and y units of the structure

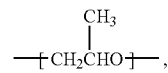

which may be present in any structural order; each of x and y may be same or different in each of the groups $R^1$, $R^2$, $R^3$, $R^4$, $R^5$ and $R^6$; x ranges from 0 to 150, inclusive; y ranges from 0 to 150, inclusive; and the sum of x and y ranges from 1 to 300, inclusive, a) said ester hem resent in the amount of from about 0.1% to about 99% by weight of the composition, and b) at least one functional ingredient present in the amount of from about 0.1% to 60% by weight of the composition;

wherein said composition is a personal care or cosmetic product.

24. The composition of claim 23, wherein said ester in accordance with the formula (I), where $R^2$ is hydrogen,

—R$^{14}$O—[ALK—O]—H or —OR$^{15}$—[ALK—O]—H; and $R^3$ and $R^4$ are independently selected from the group consisting of hydrogen, lower alkyl and halogenated lower alkyl.

25. The composition of claim 24, wherein said ester has the structure

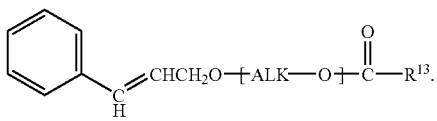

26. The composition of claim 24, wherein said ester has the structure

27. The composition of claim 26, wherein said at least one ester in PPG-3 benzyl myristate.

28. The composition of claim 26, said at least one ester is PPG-10 benzyl propionate.

29. The composition of claim 3, wherein said sunscreen active ingredient is present in the amount from about 0.1% to about 30% by weight of the composition and said ester is present in the amount between about 0.5% and about 60% by weight of the composition.

30. The composition of claim 23, wherein said functional ingredient is a sunscreen active ingredient and said ester is the ester of the formula (II).

31. A sunscreen composition comprising from about 0.5% to about 60% of an ester of alkoxylated aromatic alcohol and fatty carboxylic acid having the structure

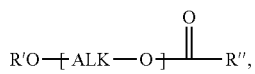

wherein R' is an organic moiety including at least one aromatic nucleus $R^N$ that may be substituted or unsubstituted, said aromatic nucleus $R_N$ having from 6 to 20 carbon atoms exclusive of, substitution and wherein R' has the structure $R_N$—$(CH_p)_n$—, where —$(CH_p)_n$— is an alkyl group, which may be straight-chain or branched, saturated or unsaturated, in which p is 0, 1, or 2, and n varies from 1 to 6 ;

R" is a fatty alkyl group, straight chain or branched, saturated or unsaturated, substituted or unsubstituted having, from 1 to 39 carbon atoms; and —[ALK—O]— is an alkoxy spacer having m number of units of the structure —$(R'''O)_m$—, which may be same or different, where m ranges from 1 to 300 and each R''' is an alkyl group, straight-chain or branched, saturated or unsaturated, substituted or unsubstituted, having from 1 to 6 carbon atoms and from about 0.1% to about 30% of a sunscreen active ingredient.

32. The sunscreen composition of claim 32, wherein said sunscreen compound selected from the group consisting of octyl methoxycinnamate, phenylbenzimidazole sulfonic acid, menthyl anthranilate, cinnamidopropyl trimonium chloride, para-aminobenzoic acid, benzophenone-1, benzophenone-2 benzophenone-3, benzophenone-4, benzophenone-5, benzophenone-6, benzophenone-8, benzophenone-12, methoxycinnamate, avobenzone, ethyl dihydroxypropyl para-aminobenzoate, glyceryl para-aminobenzoate, methyl anthranilate, octocrylene, octyl dimethyl para-aminobenzoate, octyl salicylate, zinc oxide, titanium dioxide, and red petrolatum.

33. An antiperspirant composition comprising at least one ester of alkoxylated aromatic alcohols and fatty carboxylic acids having the structure

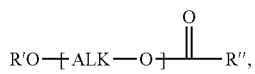

wherein R' is an organic moiety including at least one aromatic nucleus $R_N$ that may be substituted or unsubstituted, said aromatic nucleus $R_N$ having from 6 to 20 carbon atoms exclusive of substitution and wherein R' has the structure $R_N$—$(CH_p)_n$—, where —$(CH_p)_n$— is an alkyl group, which may be straight-chain or branched, saturated or unsaturated, in which p is 0, 1, or 2, and n varies from 1 to 6 or R' is a bisphenol;

R" is a fatty alkyl group, straight chain or branched, saturated or unsaturated, substituted or unsubstituted, having from 1 to 39 carbon atoms; and —[ALK—O]— is an alkoxy spacer of units of the structure —$(R'''O)_m$—, which may be same or different, where m ranges from 1 to 300 and each R''' is an alkyl group, straight-chain or branched, saturated or unsaturated, substituted or unsubstituted, having from 1 to 6 carbon atoms present in the amount of from about 0.1% to about 40% by weight of the composition, at least one antiperspirant active ingredient present in the amount of from about 1% to about 20% by weight of the composition, and at least one cyclomethicone compound present in the amount of from about 1% to about 40% by weight of the composition.

34. The composition of claim 33, wherein said at least one ester is present in the amount of from about 0.1% to about 10% by weight of the composition, at least one antiperspirant active ingredient present in the amount of from about 1% to about 15% by weight of the composition, and at least one cyclomethicone compound present in the amount of from about 1% to about 15% by weight of the composition.

35. The antiperspirant composition of claim 33, wherein said at least one enter is present in the amount of from about 1% to about 6% by weight of the composition, said at least one antiperspirant active ingredient is present in the amount of from about 1% to about 5% by weight of the composition, and said at least one cyclomethicone compound is present in the amount of from about 2% to about 10% by weight of the composition.

36. A method of improving the protection of human or animal skin or hair from radiation comprising the steps of a) providing a sunscreen composition of claim 31, and b) topically applying said sunscreen composition to said hair or skin.

37. A method of improving the protection of human or animal skin or hair from perspiration comprising the steps of a) providing a antiperspirant composition of claim 33, and b) topically applying said antiperspirant product formulation to the hair or skin.

38. The composition of claim 23, wherein said functional ingredient is an active ingredient selected from the group consisting of sunscreen active ingredients, surfactants, moisturizers, conditioners, antiseptic agents, anti-oxidants, reducing agents, antiperspirants, and fragrances.

39. The composition of claim 38, wherein said active ingredient is the sunscreen compound selected from the group consisting of octyl methoxycinnamate, phenylbenzimidazole sulfonic acid, methyl anthranilate, cinnamidopropyl trimonium chloride, para-aminobenzoic acid, benzophenone-1, benzophenon-2, benzophenone-3, benzophenone-4, benzophenone-5, benzophenone-6, benzophenone-8, benzophenone-12, methoxycinnamate, avobenzone, ethyl dihydroxypropyl para-aminobenzoate, glyceryl paraaminobenzoate, methyl anthranilate, octocrylene, octyl dimethyl para-aminobenzoate, octyl salicylate, zinc oxide, titanium dioxide and red petrolatum.

40. The composition of claim 39, wherein said personal care or cosmetic product is a topical sunscreen product formulation selected from the group consisting of a suntan lotion, a sunscreen lotion, a sunscreen spay lotion, UV-protecting shampoo, and UV-protecting hair conditioner.

41. The composition of claim 23, further comprising at least on cyclomethicone compound present in the amount of from about 1% to about 40% by weight of the composition.

42. The composition of claim 41, wherein said active ingredient is an antiperspirant.

43. The composition of claim 42, wherein said personal care or cosmetic product is a topical antiperspirant product formulation selected from the group consisting of antiperspirant stick, clear deodorant stick, antiperspirant gel and antiperspirant spray.

44. The composition of claim 23, wherein said personal care or cosmetic product is selected from the group consisting of shampoos, hair conditioners, sunscreen product formulations, antiperspirant, baby shampoos, baby bath products, hand dishwashing liquids, body washes, facial washes, and baby wipes.

45. The composition of claim 23, wherein said personal care product is in the form selected from the group consisting of microemulsion gel, emulsion, liquid, solid, cream, aerosol spray and non-aerosol spray.

46. The composition of claim 38, further comprising one or more additional ingredients selected from the group consisting of emollients, emulsifiers, humectants, softeners, lubricants, penetrants, plastisizers, solvents and co-solvents, dispersants, thickening agents, preservatives, buffers, chelating agents, foaming agents, coupling agents, proteins, salts, and oils.

47. The composition of claim 26, wherein ─[ALK─O]─ is an alkoxy spacer that includes x units of the structure ─[CH$_2$CH$_2$O]─ and y units of the structure

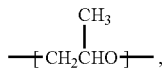

which may be present in any structural order; each of x and y may be same or different in each of the groups R$^1$, R$^2$, R$^3$, R$^4$, R$^5$ and R$^6$; x ranges from 0 to 150, inclusive; y ranges from 0 to 150, inclusive; and the sum of x and y ranges from 1 to 300, inclusive, and R$^{13}$ is an alkyl group, straight chain or branched, saturated or unsaturated, substituted or unsubstituted, containing from 1 to 39 carbon atoms.

48. The composition of claim 47, wherein x ranges from 0 to 40, inclusive, y ranges from 0 to 40, inclusive, and the sum of x and y is from 1 to 40, inclusive.

49. The composition of claim 47, wherein the sum of x and y ranges from 75 to 300, inclusive.

50. The composition of claim 47, wherein x is 0, y is 3, and R$_{13}$ contains 13 carbon atoms.

51. The composition of claim 47, wherein R$^{13}$ contains from 5 to 21 carbon atoms.

52. The composition of claim 1, wherein said aromatic nucleus and the oxygen atom of said ester carboxylic gropu are connected to said alkoxy spacer, and said fatty alkyl group is attached to the carbon atom of said ester carboxylic group.

53. The composition of claim 1, wherein the aromatic nucleus R$_N$ has 6 carbon atoms exclusive of substitution.

54. The composition of claim 1, wherein R$_N$─(CH$_p$)$_n$─ is

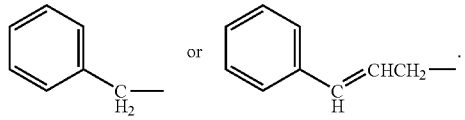

55. The composition of claim 53, wherein R"includes two of the aromatic nuclei R$_N$.

56. The composition of claim 55, wherein R"includes three of the aromatic nuclei R$_N$.

57. The composition of claim 1, wherein the aromatic nucleus R$_N$ has 10 carbon atoms exclusive of substitution.

58. The composition of claim 1, wherein said alkoxy spacer ─[ALK─O]─ includes x number of units of the structure ─[CH$_2$CH$_2$O]─ and y number of units of the structure,

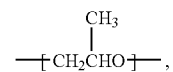

which may be present in any structural order; x ranges from 0 to 150, inclusive; and the sum of x and y, which is m, ranges from 1 to 300, inclusive.

59. The composition of claim 58, wherein x<0, y<0, and x<y.

60. The composition of claim 58, wherein x>0, y<0, and y<x.

61. The composition of claim 1, wherein R" does not include an aromatic group.

62. An ester of alkoxylated aromatic alcohol and fatty carboxylic acid having the structure

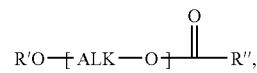

wherein R' is an organic moiety including at least one aromatic nucleus R$_N$ that may be substituted or unsubstituted, said aromatic nucleus R$_N$ having from 6 to 20 carbon atoms exclusive of substitution and wherein R' has the structure R$_N$─(CH$_p$)$_n$─, where ─(CH$_p$)$_n$─is an alkyl group, which may be straight-chain or branched, saturated or unsaturated, in which p is 0, 1, or 2, and n varies from 1 to 6;

R" is a fatty alkyl group, straight chain or branched, saturated or unsaturated, substituted or unsubstituted, having from 1 to 39 carbon atoms; and ─[ALK─O]─ is an alkoxy spacer having m number of units of the structure -(R'''O)$_m$-, which may be same of different, where m ranges from 1 to 300 and each R''' is an alkyl group, straight-chain or branched, saturated or unsaturated, substituted or unsubstituted, having from 1 to 6carbon atoms.

63. The ester of claim 62 having an armomatic nucleus, an alkoxy spacer, an ester carboxylic group, and a fatty alkyl group, wherein said aromatic nucleus and the oxygen atom of said ester carboxylic group are connected to said alkoxy spacer, and said fatty alkyl group is attached to the carbon atom of said ester carboxylic group.

64. The ester of claim 62 having a skin spread factor of less than about 10 or viscosity of less than about 20,000 cps.

65. The ester of claim 63 having one of said ester carboxylic groups.

66. The ester of claim 63 having two of said ester carboxylic groups.

67. The ester of claim 62 wherein R' is an organic moiety including at least one aromatic nucleus R$_N$ that may be substituted or unsubstituted, said aromatic nuclues R$_N$ having from 6 to 20 carbon atoms exclusive of substitution and wherein R' has the structure R$_N$-(CH$_p$)$_n$-, where -(CH$_p$)$_n$-is an alkyl group, which may be straight-chain or branched, saturated or unsaturated, in which p is 0,.1, or 2. and n varies from 1 to 6.

68. The ester of claims 62 or 67, wherein the aromatic nucleus R$_N$ has 6 carbon atoms exclusive of substitution.

69. The ester of claims 62 or 67, wherein $R_N$-$(CH_p)_n$- is

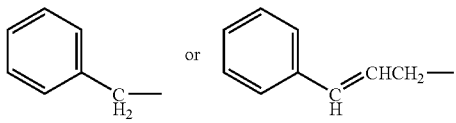

70. The ester of claim 68, wherein R' includes two of the aromatic nuclei $R_N$.
71. The ester of claim 70, wherein R' includes three of the aromatic nuclei $R_N$.
72. The ester of claims 62 or 67, wherein the aromatic nucleus $R_N$ has 10 carbon atoms exclusive of substitution.
73. The ester of claim 72, wherein $R_N$ is naphtyl.
74. The ester of claims 62 or 67, wherein said alkoxy spacer —[ALK]— includes x number of units of the structure ]ALK—O] includes x number of units of the structure,

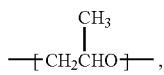

which may be present in any structural order; x ranges from 0 to 150, inclusive; y ranges from 0 to 300, inclusive.
75. The ester of claim 74, wherein m ranges from 1 to 20 inclusive.
76. The ester of claim 75, wherein x is 0.
77. The ester of claim 75, wherein y is 0.
78. The ester of claim 75, wherein x>0, y>0, and x>y.
79. The ester of claim 75, wherein x>0, y>0, and y>x.
80. The ester of claim 74, wherein m ranges from 100 to 300, inclusive.
81. The ester of claims 62 or 67, wherein R" does not include an aromatic group.
82. The ester of claims 62 or 67, wherein R" has 1 to 21 carbon atoms.
83. The ester of claim 82, wherein R" has 5 to 21 carbon atoms.
84. The ester of claim 83, wherein R" has 7 to 17 carbon atoms.
85. The ester of claims 62 or 67 produced by reacting the fatty carboxylic acid or a derivative thereof with the alkoxylated aromatic alcohol.
86. The ester of claim 85, wherein said alkoxylated aromatic alcohol has two hydroxy groups capable of reacting with said fatty carboxylic acid or said derivative thereof.
87. The ester of claim 86, wherein said fatty carboxylic acid is reacted with a stoichiometric excess of said alkoxylated aromatic alcohol.
88. The ester of claim 86, wherein said alkoxylated aromatic alcohol is reacted with a stoichiometric excess of said fatty carboxylic acid.
89. The ester of claim 85, wherein said alkoxylated aromatic alcohol has one hydroxy group capable of reacting with said fatty carboxylic acid or said derivative thereof.
90. The ester of claim 85, wherein said fatty carboxylic acid or derivative thereof contains a fatty alkyl group having 1 to 39 carbon atoms.
91. The ester of claim 90, wherein said fatty alkyl group has 5 to 21 carbon atoms.
92. The ester of claim 91, wherein said fatty alkyl group has 7 to 17 carbon atoms.
93. The ester of claim 82, wherein said fatty carboxylic acid is selected from the group consisting of myristic acid, propionic acid, behenic acid, erucic acid, montan acid, phenyl acetic, oleic acid, stearic acid, palmitic acid, coconut-oil-derived acid mixture, palm oil-derived acid mixture, and mixtures thereof.
94. The ester of claim 82, wherein said derivative of fatty carboxylic acid is selected from the group consisting of carboxylic acid anhydrides, natural oils, triglycerides, and mixtures thereof.
95. The ester of claim 83, wherein said alkoxylated aromatic alcohol is selected from the group consisting of alkoxylated benzyl alcohol, alkoxylated cynnamyl alcohol, and mixtures thereof.
96. The ester of claims 62 or 67, wherein said ester has the structure

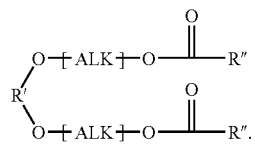

97. The ester of claim 82, wherein said ester has has the structure

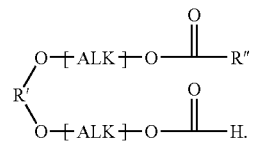

98. The ester of claim 63, wherein said fatty alkyl group is an aliphatic group containing from 1 to 39 carbon atoms.
99. An ester having the formula (I), or (II):

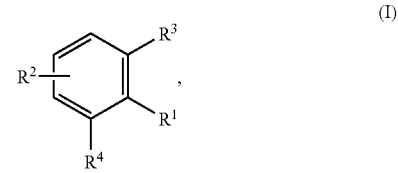

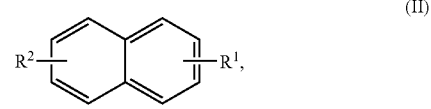

wherein $R^1$ is a group of the structure

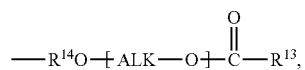

$R^2$, $R^3$, and $R^4$, which may be same or different, are each independently selected from the group consisting of hydrogen, lower alkyl, lower halogenated alkyl, hydroxy, lower alkylhydroxy, halo, lower alkoxy, a group of the structure

a group of the structure

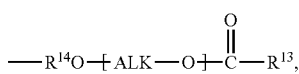

a group of the structure

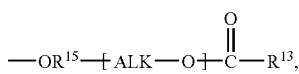

a group of the stucture —O—[ALK—O]—H,
a group of the structure —R$^{14}$O—[ALK—O]—H,
a group of the structure —OR$^{15}$—[ALK—O]—H,
a group of the structure

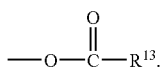

a group of the structure

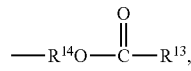

and
a group of the structure

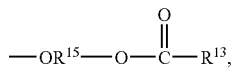

R$^{13}$, which may be same or different in each of the groups R$^1$, R$^2$, R$^3$, R$^4$, R$^5$, and R$^6$, is an alkyl group, straight chain or branched, saturated or unsaturated, substituted or unsubstituted, having 1 to 39 carbon atoms;

R$^{14}$, which may be same or different in each of the groups R$^1$, R$^2$, R$^3$, and R$^4$, is an alkyl group, straight chain or branched, saturated or unsaturated, substituted or unsubstituted, containing 1 to 6 carbon atoms;

R$^{15}$, which may be same or different in each of the groups R$^1$, R$^2$, R$^3$, and R$^4$, is an alkyl group, straight chain or branched, saturated or unsaturated, substituted or unsubstituted, containing 1 to 8 carbon atoms;

—[ALK—O]— is an alkoxy spacer that includes x units of the structure —[Ch$_2$CH$_2$O]— and y units of the structure

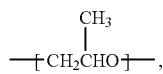

which may be present in any structural order; each of x ranges from 0 to 150, inclusive; y ranges from 0 to 150, inclusive; and the sum of x and y ranges from 1 to 300, inclusive.

100. The ester of claim 99 in accordance with the formula (I), wherein
R$^2$ is hydrogen,

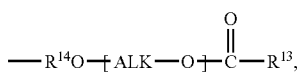

-continued

R$^{14}$ O—[ALK—O]—H or —OR$^{15}$—[ALK—O]—H; and

R$^3$ and R$^4$ are independently selected from the group consisting of hydrogen, lower alkyl and halogenated lower alkyl.

101. The ester of claim 100, wherein —R$^{14}$— is the group —(CH$_p$)$_n$—, in which p is 0, 1, or 2, and n varies from 1 to 6.

102. The ester of claim 100, wherein R$^2$ is R$^{14}$O—[ALK—O]—H.

103. The ester of claim 100, wherein R$^2$ is hydrogen.

104. The ester of claim 103, wherein R$^3$ and R$^4$ are independently hydrogen, methyl, ethyl or propyl.

105. The ester of claim 104 having the structure

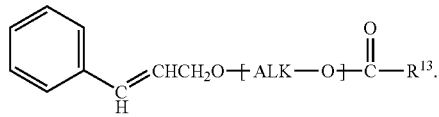

106. The ester of claim 104 having the structure

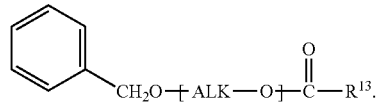

107. The ester of claim 99, wherein x is 0, y is 3, and R$^{13}$ has 13 carbon atoms.

108. The ester of claim 99, wherein x is 0, y is 10, and R$^{13}$ has 3 carbon atoms.

109. The ester of claim 100, wherein R$^2$ has the structure

110. The ester of claim 100, wherein R$^2$ has the structure —OR$^{15}$—[ALK—O]—H.

111. The ester of claim 100, wherein R$^2$ is hydrogen.

112. The ester of claim 99 in accordance with the formula (II), wherein R$^2$ is hydrogen,

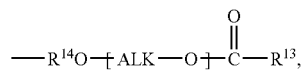

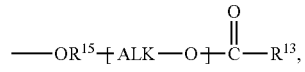

—R$^{14}$O—[ALK—O]—H or —OR$^{15}$—[ALK—O]—H.

113. The ester of claim 112 having the structure

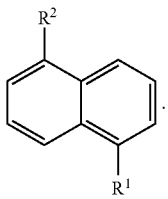

114. The ester of claim 112 having the structure

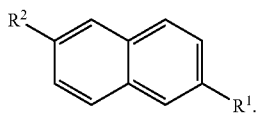

115. The ester of claim 112 having the structure

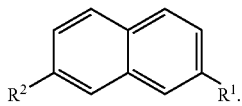

116. The ester of claim 112, wherein $R^2$ is hydrogen.

117. The ester of claim 112, wherein —$R^{14}$— is the group —$(CH_p)_n$—, in which p is 0, 1, or 2, and n varies from 1 to 6.

118. The ester of claim 99 in accordance with the formula (III), wherein $R^6$ is —[ALK—O]—H or

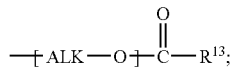

$R^7$ is hydrogen, methyl or trifluoromethyl; $R^8$ is hydrogen, methyl, trifluoromethyl, —$CHCl_2$ or

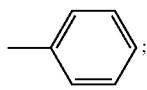

and $R^9$, $R^{10}$, $R^{11}$, and $R^{12}$ are independently hydrogen or methyl.

119. The ester of claim 99, wherein $R^{13}$ has from 1 to 21 carbon atoms.

120. The ester of claim 119, wherein $R^{13}$ has from 5 to 21 carbon atoms.

121. The ester of claim 120, wherein $R^{13}$ has from 7 to 17 carbon atoms.

122. The ester of claim 99, wherein x ranges from 0 to 20 and y ranges from 0 to 20.

123. The ester of claim 99, wherein the sum of x and y ranges from 1 to 20, inclusive.

124. The ester of claim 99, wherein the sum of x and y range from 100 to 300, inclusive.

125. An ester having the formula

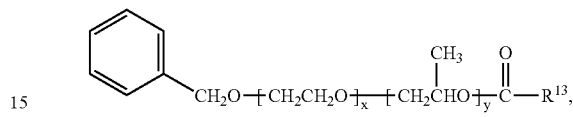

wherein $R^{13}$ is a alkyl group, straight chain or branched, saturated or unsaturated, substituted or unsubstituted, containing from 1 to 39 carbon atoms, x ranges from 0 to 150, inclusive, y ranges from 0 to 150, inclusive and the sum of x and y ranges from 1 to 300, inclusive.

126. The ester of claim 125, wherein x ranged from 0 to 40, inclusive, y ranges from 0 to 40, inclusive, and the sum of x is from 1 to 40, inclusive.

127. The ester of claim 126, wherein x ranges from 0 to 30, inclusive, y ranges from 0 to 30, inclusive, and the sum of x and y is from 1 to 30, inclusive.

128. The ester of claim 127, wherein x ranges from 0 to 20, inclusive, y ranges from 0 to 20, inclusive.

129. The ester of claim 125, wherein the sum of x and y ranges from 75 to 300, inclusive.

130. The ester of claim 125, wherein the sum of x and y ranges from 100 to 300, inclusive.

131. The ester of claim 125, wherein x is 0, y is 3, and $R^{13}$ contains 13 carbon atoms.

132. The ester of claim 125, wherein x is 0, y is 10, and $R^{13}$ contains 3 carbon atoms.

133. The ester of claim 125, wherein $R^{13}$ contains from 5 to 21 carbon atoms.

134. The ester of claim 125, wherein $R^{13}$ contains from 5 to 17 carbon atoms.

135. The ester of claim 100, wherein $R^2$

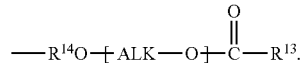

* * * * *

UNITED STATES PATENT AND TRADEMARK OFFICE
CERTIFICATE OF CORRECTION

| | | |
|---|---|---|
| PATENT NO. | : 7,217,424 B2 | Page 1 of 1 |
| APPLICATION NO. | : 10/272556 | |
| DATED | : May 15, 2007 | |
| INVENTOR(S) | : Abel G. Pereira, Christopher Westergom and Patrick Obukowho | |

It is certified that error appears in the above-identified patent and that said Letters Patent is hereby corrected as shown below:

On the Title page of Patent No. 7,217,424, please insert -- This patent is subject to a terminal disclaimer --.

Signed and Sealed this

Twenty-third Day of September, 2008

JON W. DUDAS
*Director of the United States Patent and Trademark Office*